(12) United States Patent
Esaki et al.

(10) Patent No.: US 8,286,629 B2
(45) Date of Patent: Oct. 16, 2012

(54) NEBULIZER AND INHALATION AID USED THEREFOR

(75) Inventors: Masayuki Esaki, Kyoto (JP); Kentaro Mori, Kyoto (JP); Makoto Tabata, Kyoto (JP); Kei Asai, Kyoto (JP); Yosuke Fujii, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 294 days.

(21) Appl. No.: 12/866,082

(22) PCT Filed: Feb. 25, 2009

(86) PCT No.: PCT/JP2009/053401
§ 371 (c)(1),
(2), (4) Date: Aug. 4, 2010

(87) PCT Pub. No.: WO2009/113395
PCT Pub. Date: Sep. 17, 2009

(65) Prior Publication Data
US 2010/0319687 A1 Dec. 23, 2010

(30) Foreign Application Priority Data
Mar. 13, 2008 (JP) .................................. 2008-064579

(51) Int. Cl.
*A61M 11/00* (2006.01)

(52) U.S. Cl. .......... 128/200.21; 128/200.14; 128/200.18
(58) Field of Classification Search ........................ None
See application file for complete search history.

(56) References Cited

U.S. PATENT DOCUMENTS

| | | |
|---|---|---|
| 5,584,285 A | 12/1996 | Salter et al. |
| 2003/0136399 A1 | 7/2003 | Foley et al. |
| 2008/0223361 A1 | 9/2008 | Nieuwstad |

FOREIGN PATENT DOCUMENTS

| | | |
|---|---|---|
| JP | A-7-503633 | 4/1995 |
| JP | A-2001-517979 | 10/2001 |
| JP | A-2003-126255 | 5/2003 |
| JP | B2-3802929 | 8/2006 |
| JP | A-2007-97830 | 4/2007 |
| WO | WO 98/41255 A2 | 9/1998 |
| WO | WO 03/053500 A1 | 7/2003 |

OTHER PUBLICATIONS

International Search Report issued in International Patent Application No. PCT/JP2009/053401, dated Apr. 14, 2009 (with English translation).

*Primary Examiner* — Jackie Ho
*Assistant Examiner* — Joshua Lee
(74) *Attorney, Agent, or Firm* — Oliff & Berridge, PLC

(57) ABSTRACT

A nebulizer includes a nebulizer body a relay pipe. The nebulizer body includes a connection portion that has an aerosol lead-out port to lead out aerosol, and the relay pipe includes a connection portion that has an aerosol introduction port to introduce the aerosol. The nebulizer body the relay pipe can take a first connection state in which the relay pipe detachably connected to the nebulizer body and a second connection state in which the relay pipe is connected to the nebulizer body so as to be not able to be detached from the nebulizer body. In the first connection state, the aerosol introduction port and the aerosol lead-out port are communicated with each other. In the second connection state, the aerosol lead-out port is blocked by a blocking portion provided in the relay pipe. Therefore, the nebulizer in which reuse of the nebulizer body or relay pipe is simply prohibited after the usage can be provided by the configuration.

13 Claims, 31 Drawing Sheets

NEBULIZER AND INHALATION AID USED THEREFOR

TECHNICAL FIELD

The present invention relates to a nebulizer, which includes a nebulizer body in which an aerosol is produced and an inhalation aid that is used while attached to the nebulizer body in order that a user inhales the aerosol produced in the nebulizer body, and the inhalation aid.

BACKGROUND ART

The nebulizer atomizes a liquid such as a medical solution that cures diseases such as a bronchus, water, and saline water to produce the aerosol. The aerosol produced by the nebulizer is inhaled from a mouth or a nose by the user and taken into a body. Recently, in one of new methods for utilizing the nebulizer, a vaccine for preventing measles is aerosolized with the nebulizer, and the aerosolized vaccine is administered to the body through the mouth or nose of the user.

Usually the inhalation aid is attached to the nebulizer in order to facilitate the inhalation of the aerosol. A flow passage is provided in the inhalation aid in order to convey the aerosol, the inhalation aid is attached to the nebulizer body in the usage of the nebulizer, and the user inhales the aerosol through the inhalation aid.

There are various types of inhalation aids. The types of the inhalation aids are roughly classified into a mouthpiece, a nosepiece, a mask, and a relay pipe. The mouthpiece is used such that the user holds the mouthpiece in user's mouth to inhale the aerosol from the mouth. The nosepiece is used such that the user places the nosepiece in a nostril to inhale the aerosol. As to the mask, the user puts the mask so as to cover the mouth and nose therewith and inhales the aerosol from the mouth and nose. The relay pipe is used to relay the mouthpiece, the nosepiece, the mask, and the like and an aerosol lead-out port of the nebulizer body if needed. The optimum inhalation aid is appropriately selected and used according to a kind of the inhaled liquid or the user who inhales the liquid.

Japanese Unexamined Patent Publication No. 2003-126255 (Patent Document 1), Published Japanese Translation of PCT application No. 7-503633 (Patent Document 2), and Japanese Unexamined Patent Publication No. 2007-97830 (Patent Document 3) can be cited as examples of the documents that disclose the nebulizers including various types of the inhalation aids.

When the nebulizer is used in the administration of the vaccine, a combination of the mask and the relay pipe is suitably selected as the inhalation aid based on a usage environment, a usage condition, and the like. This is because usually the administration of vaccine is targeted in mass immunization. That is, in the usage environment in which many users use the nebulizer one after another for a short time, from the hygiene standpoint, particularly from the standpoint of prevention of secondary infection through the inhalation aid (a user is infected with a certain pathogen from another user infected with the pathogen through the inhalation aid), preferably the inhalation aid is formed by the combination of the disposable type mask and the relay pipe that connects the disposable type mask to the nebulizer body. Therefore, the vaccine can be administered while the disposable type mask is replaced and connected to the relay pipe in each time of the usage, generation of the secondary infection can effectively be prevented, and the nebulizer becomes excellent in handling convenience and economic efficiency.

[Patent Document 1] Japanese Unexamined Patent Publication No. 2003-126255
[Patent Document 2] Published Japanese Translation of PCT application No. 7-503633
[Patent Document 3] Japanese Unexamined Patent Publication No. 2007-97830

DISCLOSURE OF THE INVENTION

Problems to be Solved by the Invention

As described above, the usage of the disposable type mask is studied when the nebulizer is used in the administration of the vaccine. However, the usage of the disposable type mask cannot completely prevent the generation of the secondary infection. For example, when a user coughs or sneezes during the administration of the vaccine, there is a risk that saliva or snivel does not remain in the mask but reaches in the relay pipe or nebulizer body. In such cases, possibly another user who takes the vaccine with the nebulizer subsequently inhales the saliva or snivel of the previous user along with the vaccine.

At this point, usually the nebulizer can repeatedly be used by cleaning and sterilizing the nebulizer body and the relay pipe in each time of the usage. However, in the usage environment in which many users use the nebulizer one after another like the mass immunization, the cleaning and sterilizing work cannot be performed every time one user uses the nebulizer body and the relay pipe. Accordingly, from the hygiene standpoint, preferably the nebulizer body and relay pipe are disposed of after used to some extent (for example, after tens users take the administration of the vaccine). When the user coughs or sneezes during the administration of the vaccine, preferably the usage of the nebulizer is immediately stopped and disposed of.

However, even if the nebulizer body and the relay pipe are intended to be disposed of after the usage, possibly an assistant who has insufficient knowledge reuses the nebulizer body and the relay pipe without knowing that the nebulizer body and the relay pipe should be disposed of after the usage, or possibly the assistant mistakenly reuses the nebulizer body and the relay pipe although they know the nebulizer body and the relay pipe should be disposed of, In some cases, possibly the malicious third party recovers the nebulizer body and relay pipe, which are disposed of, and sells the nebulizer body and relay pipe to the assistant again under the guise of brand-new. Accordingly, a device is required to be not able to reuse the nebulizer body and the relay pipe after the usage.

In view of the foregoing, an object of the invention is to provide a nebulizer in which the reuse of the nebulizer body and the inhalation aid can simply be prohibited after the usage and the inhalation aid whose reuse can simply be prohibited.

Means for Solving the Problem

In accordance with a first aspect of the invention, there is provided a nebulizer including: a nebulizer body in which aerosol is produced; and an inhalation aid that is used while attached to the nebulizer body in order that a user inhales the aerosol produced in the nebulizer body, wherein the nebulizer body includes: a reservoir portion in which a liquid is reserved; a compressed air introduction port that introduces compressed air; an outer air introduction port that introduces outer air; an aerosol producing portion that atomizes the liquid reserved in the reservoir portion into atomized particles using the compressed air introduced from the compressed air introduction port and produces aerosol by providing the atomized particles to the outer air introduced from the outer air introduction port; and an aerosol lead-out port that leads out the aerosol produced in the aerosol producing portion, the inhalation aid includes: an aerosol introduction port that introduces the aerosol; and an aerosol ejection port that ejects the aerosol introduced from the aerosol introduction port toward a user, the nebulizer body and the inhalation aid are detachably connected such that the aerosol lead-out port and the aerosol introduction port are communicated, the nebulizer further includes a blocking portion that can block at least one of the compressed air introduction port, the outer air introduction port, the aerosol lead-out port, the aerosol introduction port, and the aerosol ejection port, and the blockage of the blocking portion cannot substantially be released once the blockage is performed by the blocking portion.

In the above first aspect, the blocking portion is formed by a cap-shaped member that is independently provided as another component while separated from the nebulizer body and the inhalation aid.

In the above first aspect, the blocking portion is formed by a cap-shaped member that is provided in one of the nebulizer body and the inhalation aid. The blocking portion is attached to one of the nebulizer body and the inhalation aid with a deformable coupling portion interposed therebetween.

In the above first aspect, the nebulizer includes a latching mechanism that includes a latching pawl portion provided in one of the nebulizer body and the blocking portion and a latching step portion provided in the other of the nebulizer body and the blocking portion, the latching pawl portion is fitted in the latching step portion while being not able to be detached from the latching step portion, and the blocking portion is connected to the nebulizer body while being not able to be detached from the nebulizer body, whereby the blockage of the blocking portion cannot substantially be released.

In the above first aspect, the nebulizer includes a latching mechanism that includes a latching pawl portion provided in one of the inhalation aid and the blocking portion and a latching step portion provided in the other of the inhalation aid and the blocking portion, the latching pawl portion is fitted in the latching step portion while being not able to be detached from the latching step portion, and the blocking portion is connected to the inhalation aid while being not able to be detached from the inhalation aid, whereby the blockage of the blocking portion cannot substantially be released.

In accordance with a second aspect of the invention, there is provided a nebulizer including: a nebulizer body in which aerosol is produced; and an inhalation aid that is used while attached to the nebulizer body in order that a user inhales the aerosol produced in the nebulizer body, wherein the nebulizer body includes: a reservoir portion in which a liquid is reserved; a compressed air introduction port that introduces compressed air; an outer air introduction port that introduces outer air; an aerosol producing portion that atomizes the liquid reserved in the reservoir portion into atomized particles using the compressed air introduced from the compressed air introduction port and produces aerosol by providing the atomized particles to the outer air introduced from the outer air introduction port; and an aerosol lead-out port that leads out the aerosol produced in the aerosol producing portion, the inhalation aid includes: an aerosol introduction port that introduces the aerosol; and an aerosol ejection port that ejects the aerosol introduced from the aerosol introduction port toward a user, the nebulizer body and the inhalation aids take a first connection state in which the inhalation aid is detachably connected to the nebulizer body and a second connection state in which the inhalation aid is connected to the nebulizer body while being not able to be detached from the nebulizer body, the aerosol introduction port and the aerosol lead-out port are communicated in the first connection state, and at least one of the compressed air introduction port, the outer air introduction port, and the aerosol lead-out port is blocked by the inhalation aid in the second connection state.

In the above second aspect, a cap-shaped member that blocks one of the compressed air introduction port, the outer air introduction port, and the aerosol lead-out port in the second state is provided in the inhalation aid.

In the above second aspect, the nebulizer includes a latching mechanism that includes a latching pawl portion provided in one of the nebulizer body and the inhalation aid and a latching step portion provided in the other of the nebulizer body and the inhalation aid, the latching pawl portion is fitted in the latching step portion while being not able to be detached from the latching step portion in the second connection state, whereby the inhalation aid is connected to the nebulizer body while being not able to be detached from the nebulizer body.

In accordance with a third aspect of the invention, there is provided an inhalation aid that is used while detachably attached to the nebulizer body in order that a user inhales the aerosol produced in the nebulizer body, the inhalation aid including: a aerosol introduction port that introduces aerosol from the nebulizer body; an aerosol ejection port that ejects the aerosol introduced from the aerosol introduction port toward the user; and a blocking portion that can block at least one of the aerosol introduction port and the aerosol ejection port, and the blockage of the blocking portion cannot substantially be released once the blockage is performed by the blocking portion.

In the above third aspect, the blocking portion is formed by a cap-shaped member that is independently provided as another component while separated from the inhalation aid.

In the above third aspect, the blocking portion is attached to the inhalation aid with a deformable coupling portion interposed therebetween.

In the above third aspect, the nebulizer further includes a latching mechanism that includes a latching pawl portion provided in one of the blocking portion and a portion except the blocking portion and a latching step portion provided in the other of the blocking portion and the portion except the blocking portion, the latching pawl portion is fitted in the latching step portion while being not able to be detached from the latching step portion, and the blocking portion is connected to the portion except the blocking portion while being not able to be detached from the portion except the blocking portion, whereby the blockage of the blocking portion cannot substantially be released.

Effect of the Invention

According to the invention, the reuse of the nebulizer body and inhalation aid can simply be prohibited after the usage. Therefore, the generation of the health problem such as the secondary infection can be prevented before happens by utilizing the nebulizer and the inhalation aid.

Figure 1:
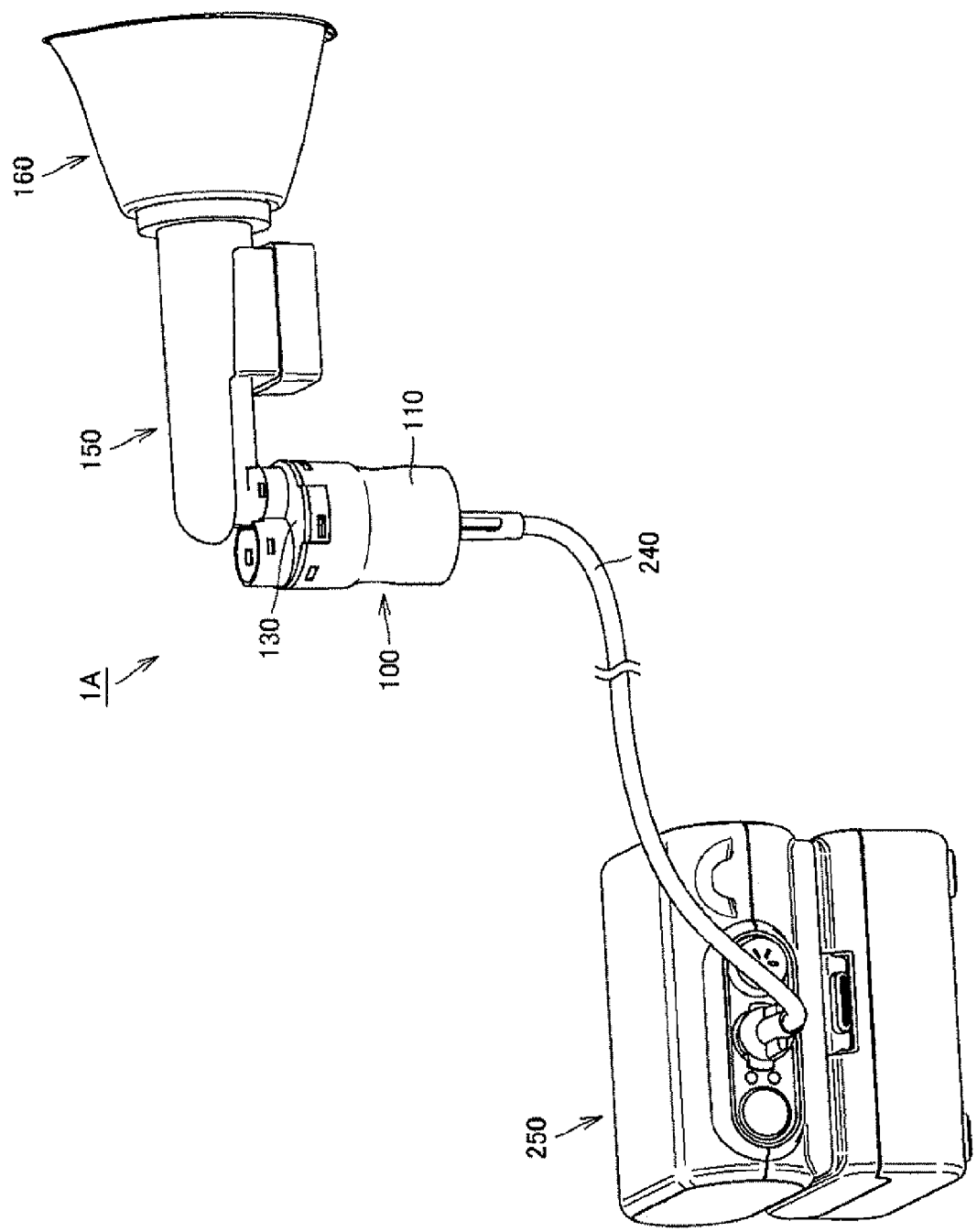
FIG. 1 is a perspective view illustrating an appearance structure in a usage state of a nebulizer according to a first embodiment of the invention.

DESCRIPTION OF SYMBOLS 1A to 1D nebulizer
100 nebulizer body
101 outer air introduction port
102 introduction passage
103 conveyance passage
110 case body
112 latching groove
114 third connection portion
114a compressed air introduction port
114b latching projection
115 compressed air introduction pipe portion
116 reservoir portion
120 atomization portion forming body
122 baffle
124 suction liquid pipe forming portion
130 flow passage forming body
131 latching projection
132 first connection portion
132a aerosol lead-out port
132b latching projection
133 second connection portion
133a upper opening portion
133b latching hole portion
134 suction pipe portion
140 cap body
141 hole
142 valve body
143 projection
150 relay pipe
151 cylindrical portion
152 fourth connection portion
152a aerosol introduction port 152b latching projection
153 fifth connection portion
153a aerosol ejection port
154a conveyance passage
154b discharge passage
155 partition wall
155a projection
156 ejection portion
156a filter
156b cover body
157 sixth connection portion
157a blocking portion
158 seventh connection portion
158a latching projection
160 mask
161 wall portion
162 relay-pipe-side opening end
162a relay-pipe-side opening portion
163 user-side opening end
163 user-side opening portion
170 blocking member
171 cover portion
172 cylindrical wall portion
173 latching projection
174 coupling portion
175 latching hole portion
180 blocking member
181 cover portion
182 cylindrical wall portion
183 latching projection
184 coupling portion
185 latching hole portion
190 blocking member
191 cover portion
192 cylindrical wall portion
193 latching hole portion
194 coupling portion
200A and 200B backflow prevention member
201 frame body
201a groove
202 projection
203 fixing member
205 valve body
206 first valve portion
207 second valve portion
208 hole
212 fixing member
216 and 217 valve body
240 tube
250 compressor
300 liquid

BEST MODES FOR CARRYING OUT THE INVENTION

Embodiments of the invention will be described in detail with reference to the drawings. In the following embodiments, a nebulizer that is suitably used in a usage environment such as mass immunization and an inhalation aid thereof will specifically be described by way of example.

First Embodiment

Figure 2:
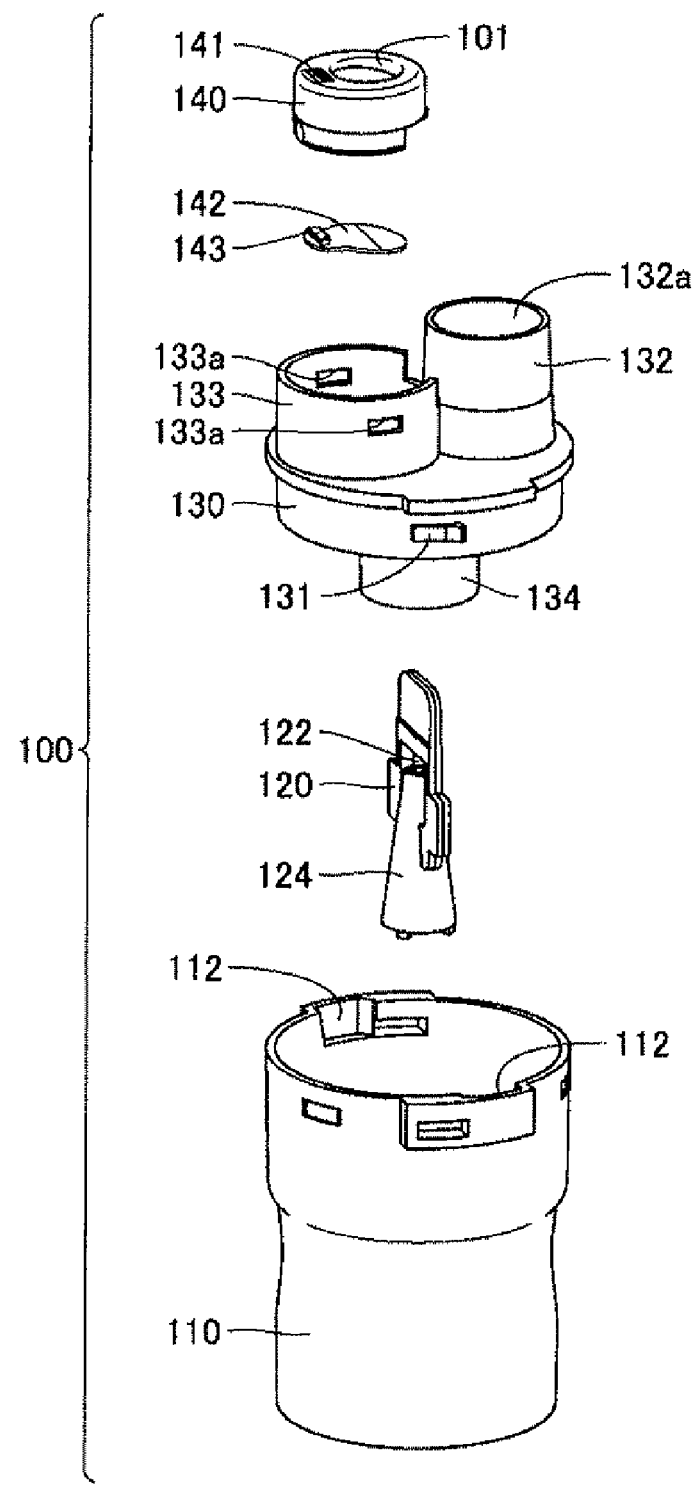
FIG. 2 is an exploded perspective view illustrating an assembly structure of a nebulizer body of FIG. 1.
Figure 3:
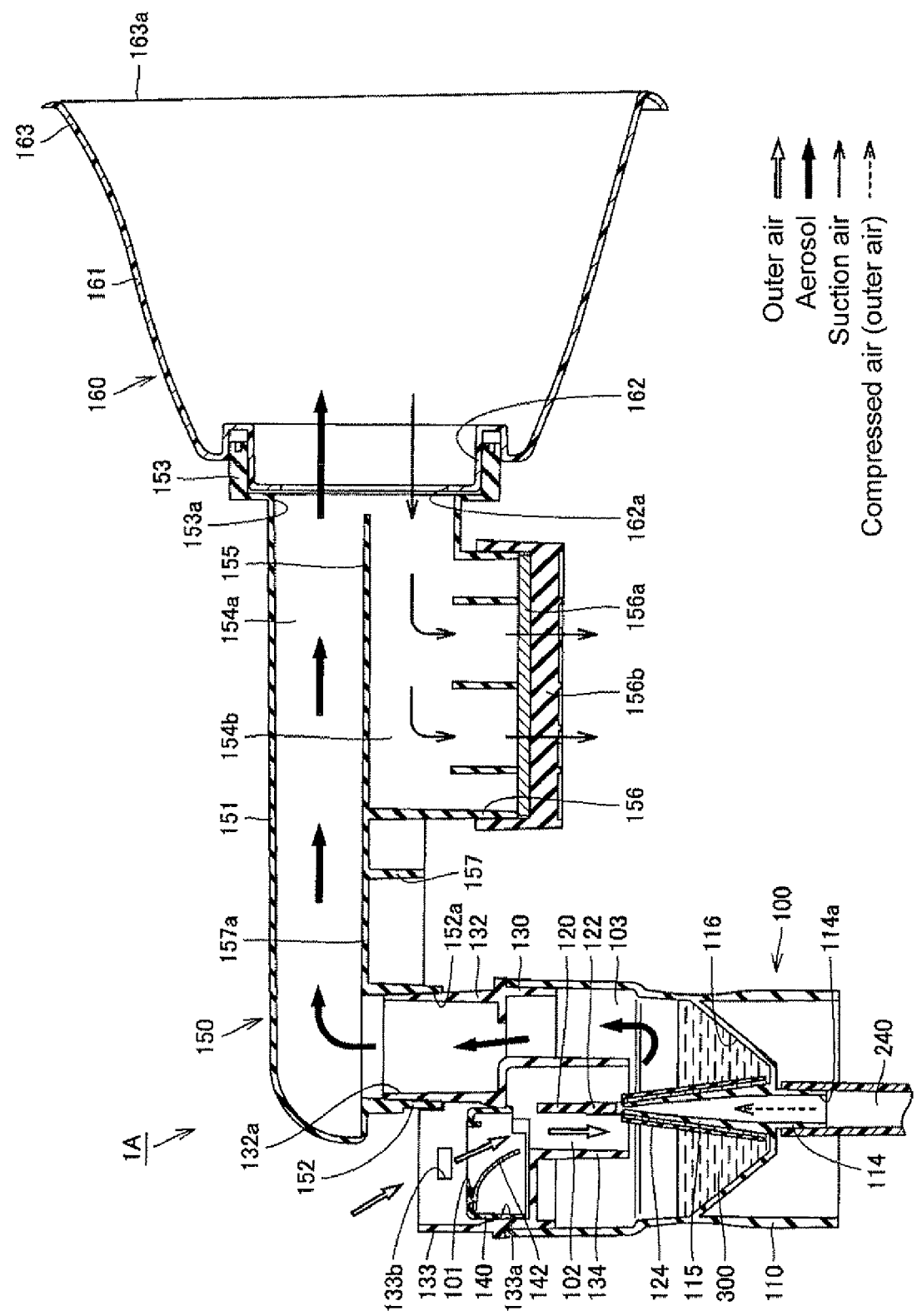
FIG. 3 is a longitudinal sectional view illustrating an internal structure of the nebulizer of FIG. 1.
Figure 4:
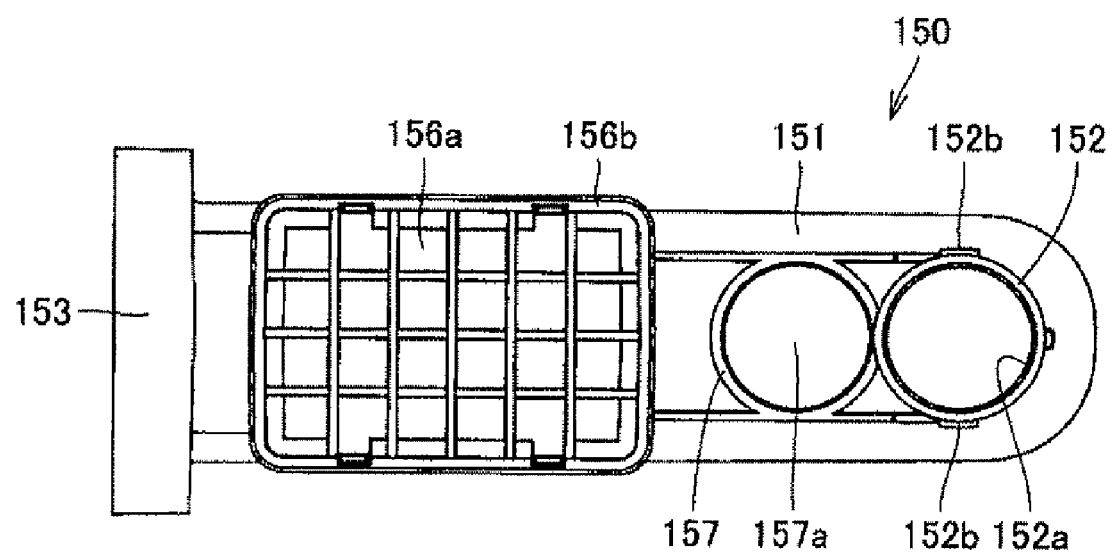
FIG. 4 is a bottom view of a relay pipe of FIG. 1.

FIG. 1 is a perspective view illustrating an appearance structure in a usage state of a nebulizer according to a first embodiment of the invention, and FIG. 2 is an exploded perspective view illustrating an assembly structure of a nebulizer body of FIG. 1. FIG. 3 is a longitudinal sectional view illustrating an internal structure of the nebulizer of FIG. 1, and FIG. 4 is a bottom view of a relay pipe of FIG. 1. First a structure of a nebulizer 1A of the first embodiment will be described with reference to FIGS. 1 to 4.

As illustrated in FIG. 1, the nebulizer 1A includes a nebulizer body 100, a relay pipe 150 that is of an inhalation aid connected to the nebulizer body 100, a mask 160 that is of an inhalation aid connected to the relay pipe 150, a tube 240 whose one end is connected to the nebulizer body 100, and a compressor 250 that is connected to the other end of the tube 240.

The compressor 250 is a device that produces compressed air, and the compressor 250 sends the compressed air to the nebulizer body 100 through the tube 240 having flexibility. The nebulizer body 100 produces aerosol therein, and the mask 160 causes a user to efficiently suck the aerosol produced by the nebulizer body 100. The relay pipe 150 conveys the aerosol produced by the nebulizer body 100 to the mask 160.

As illustrated in FIG. 2, the nebulizer body 100 includes a case body 110, an atomization portion forming body 120, a flow passage forming body 130, a cap body 140, and a valve body 142. The case body 110 has a cylindrical shape with a bottom, and the atomization portion forming body 120 is accommodated and disposed in the case body 110. The flow passage forming body 130 is attached to an upper portion of the case body 110 so as to block an upper opening of the case body 110. The cap body 140 is attached to a predetermined position in an upper surface of the flow passage forming body 130. The valve body 142 is attached to the cap body 140. The case body 110, the atomization portion forming body 120, the flow passage forming body 130, and the cap body 140 are produced by injection molding using a resin material and the like.

The case body 110, the atomization portion forming body 120, the flow passage forming body 130, the cap body 140, and the valve body 142 are used while assembled in one another. The assembly is performed by so-called fixed fitting, in which these components cannot be taken apart once are assembled, such that the components can be neither taken apart nor reused after the usage.

A pair of L-shape latching grooves 112 is provided in a circumferential direction at an upper predetermined position in a circumferential surface of the case body 110. A pair of latching projections 131 is provided in the circumferential direction at a predetermined position in an outer circumferential surface of the flow passage forming body 130. The flow passage forming body 130 is fitted in the upper opening of the case body 110, and the flow passage forming body 130 is rotated relative to the case body 110, whereby the latching grooves 112 and the latching projections 131 are latched while being not able to be detached.

The atomization portion forming body 120 includes a baffle 122 and a suction liquid pipe forming portion 124. The baffle 122 has a columnar shape and is located in an upper portion of the atomization portion forming body 120. The suction liquid pipe forming portion 124 is formed by a truncated-conical cylindrical body whose leading end is opened, and the suction liquid pipe forming portion 124 is located in a lower portion of the atomization portion forming body 120. The leading end of the suction liquid pipe forming portion 124 is disposed at a lower end of the baffle 122 with a predetermined distance while facing the baffle 122.

The flow passage forming body 130 is a member corresponding to a cover of the case body 110. The flow passage forming body 130 includes a first connection portion 132 that includes an aerosol lead-out port 132a, a second connection portion 133 that includes an upper opening portion 133a (see FIG. 3), and a suction pipe portion 134. The first connection portion 132 and the second connection portion 133 are projected upward from the upper surface of the flow passage forming body 130, respectively. The suction pipe portion 134 is projected downward from the lower surface of the flow passage forming body 130. A pair of latching hole portions 133b constituting a latching step portion is provided in the circumferential surface of the second connection portion 133.

The upper surface of the cap body 140 includes an outer air introduction port 101, and the cap body 140 is a member corresponding to a cover of the upper opening portion 133a of the flow passage forming body 130. The valve body 142 is attached from below to the cap body 140 so as to block the outer air introduction port 101. A projection 143 is provided in the valve body 142, and the valve body 142 is attached to the cap body 140 by fitting the projection 143 in a hole 141 made in the cap body 140. Although detailed description is omitted, the cap body 140 is attached while being not able to be detached from the flow passage forming body 130.

Then the structure of the nebulizer 1A in the usage state will be described in detail with reference to FIG. 3. As illustrated in FIG. 3, a third connection portion 114 is projected downward in a bottom surface of the case body 110. In the third connection portion 114, a compressed air introduction port 114a is provided in order to introduce compressed air sent from the compressor 250 into the case body 110. The tube 240 is connected to the third connection portion 114. A compressed air introduction pipe portion 115 that is tapered into a truncated conical shape is projected upward in the bottom surface of the case body 110 while connected to the third connection portion 114. The baffle 122 of the atomization portion forming body 120 is disposed in the upper leading end portion of the compressed air introduction pipe portion 115 while facing the compressed air introduction pipe portion 115. A reservoir portion 116 is provided around a portion in which the compressed air introduction pipe portion 115 of the case body 110 is formed. A liquid 300 such as water, saline water, and a medical solution and vaccine which heal diseases such as a bronchus is temporarily reserved in the reservoir portion 116.

The suction liquid pipe forming portion 124 of the atomization portion forming body 120 is disposed from above while facing the compressed air introduction pipe portion 115. A suction liquid pipe is formed by a gap between the suction liquid pipe forming portion 124 and the compressed air introduction pipe portion 115, and the liquid 300 reserved in the reservoir portion 116 reaches a neighborhood of an atomization portion by negative pressure action generated by blowing of the compressed air.

The atomization portion is formed between the compressed air introduction pipe portion 115 and the baffle 122. In the atomization portion, the compressed air is blown toward the baffle 122 from the upper leading end portion of the compressed air introduction pipe portion 115. At this point, the liquid 300 sucked up to the neighborhood of the atomization portion by the negative pressure action generated in the atomization portion is brought up to the atomization portion by the negative pressure action and blown toward the baffle 122 along the compressed air. Thanks to the action, the liquid 300 collides with the baffle 122 to become fine liquid droplets and atomized particles, and the atomized particles are given to outer air (including outer air introduced by the compressor and outer air introduced from the outer air introduction port 101, described later, based on user's suction operation) introduced into the case body 110, thereby generating the aerosol in the atomization portion.

The flow passage forming body 130 to which the cap body 140 is attached is located above the atomization portion forming body 120. In the flow passage forming body 130, the suction pipe portion 134 provided in the lower portion of the flow passage forming body 130 is disposed so as to cover the baffle 122 of the atomization portion forming body 120 therewith. A space in the case body 110 is partitioned by the flow passage forming body 130 to form a flow passage through which the air current flows. More particularly, the space in the case body 110 is partitioned into a central portion and a circumferential edge portion by the suction pipe portion 134 of the flow passage forming body 130, and the introduction passage 102 and the conveyance passage 103 are formed by the central portion and the circumferential edge portion, respectively.

As described above, the first connection portion 132 and the second connection portion 133 are located in the upper portion of the flow passage forming body 130. The aerosol lead-out port 132a provided in the first connection portion 132 is communicated with the conveyance passage 103. The outer air introduction port 101 provided in the second connection portion 133 is communicated with the introduction passage 102. Therefore, when the user performs a suction operation, the outer air is taken in the case body 110 through the outer air introduction port 101 by the negative pressure action generated in the case body 110, and the outer air is introduced to the atomization portion through the introduction passage 102. The user performs the suction operation, whereby the aerosol generated in the atomization portion reaches the aerosol lead-out port 132a through the conveyance passage 103 to lead out the aerosol to the outside of the case body 110. Because the valve body 142 that is of the check valve is attached to the outer air introduction port 101 as described above, the aerosol does not leak from the outer air introduction port 101.

Then the structure of the relay pipe 150 will be described with reference to FIGS. 3 and 4. As illustrated in FIG. 3, the relay pipe 150 includes a long cylindrical portion 151, and a conveyance passage 154a is provided in the cylindrical portion 151 in order to convey the aerosol. A fourth connection portion 152 including an aerosol introduction port 152a is provided at rear end of the cylindrical portion 151, and a fifth connection portion 153 including an aerosol ejection port 153a is provided at a front end of the cylindrical portion 151. The fourth connection portion 152 is projected downward from the lower surface of the cylindrical portion 151, and the fifth connection portion 153 is projected forward from the front surface of the cylindrical portion 151. A pair of latching projections 152b constituting a latching pawl portion is provided in the circumferential surface of the fourth connection portion 152.

Below a portion closer to the front end of the cylindrical portion 151, a discharge passage 154b that discharges suction air is provided in parallel with the aerosol conveyance passage 154a. The conveyance passage 154a and the discharge passage 154b are partitioned by a partition wall 155 provided in the cylindrical portion 151. A suction air ejection portion 156 is provided below the discharge passage 154b, and a filter 156a is provided in the ejection portion 156. The filter 156a collects the aerosol contained in the suction air and prevents the aerosol from leaking to the outside. A cover body 156b in which plural openings are formed is attached to the ejection portion 156 provided below the cylindrical portion 151, thereby assembling the filter 156a. The cover body 156b is also attached to the cylindrical portion 151 by the so-called fixed fitting.

A sixth connection portion 157 including a blocking portion 157a is provided in the portion closer to the rear end of the cylindrical portion 151 and the lower surface of the cylindrical portion 151 adjacent to the portion in which the fourth connection portion 152 is provided. The sixth connection portion 157 is projected downward from the lower surface of the cylindrical portion 151, and the blocking portion 157a is formed by the lower surface of the cylindrical portion 151. The relay pipe 150 is produced by injection molding using a resin material and the like.

Then the structure of the mask 160 will be described with reference to FIG. 3. The mask 160 is formed into a bowl shape while the mask 160 has a space therein. The mask 160 includes a relay-pipe-side opening end 162 that includes a relay-pipe-side opening portion 162a, a user-side opening end 163 that includes a user-side opening portion 163, and a curved wall portion 161 that defines the space between the relay-pipe-side opening end 162 and the user-side opening end 163. The relay-pipe-side opening end 162 is a region that is connected to the fifth connection portion 132 of the relay pipe in the usage state, and the user-side opening end 163 is a region that is held against a user's face so as to cover the mouth and nose therewith in the usage state. For example, the mask 160 is produced by sheet molding (vacuum molding) using a resin material.

Figure 5:
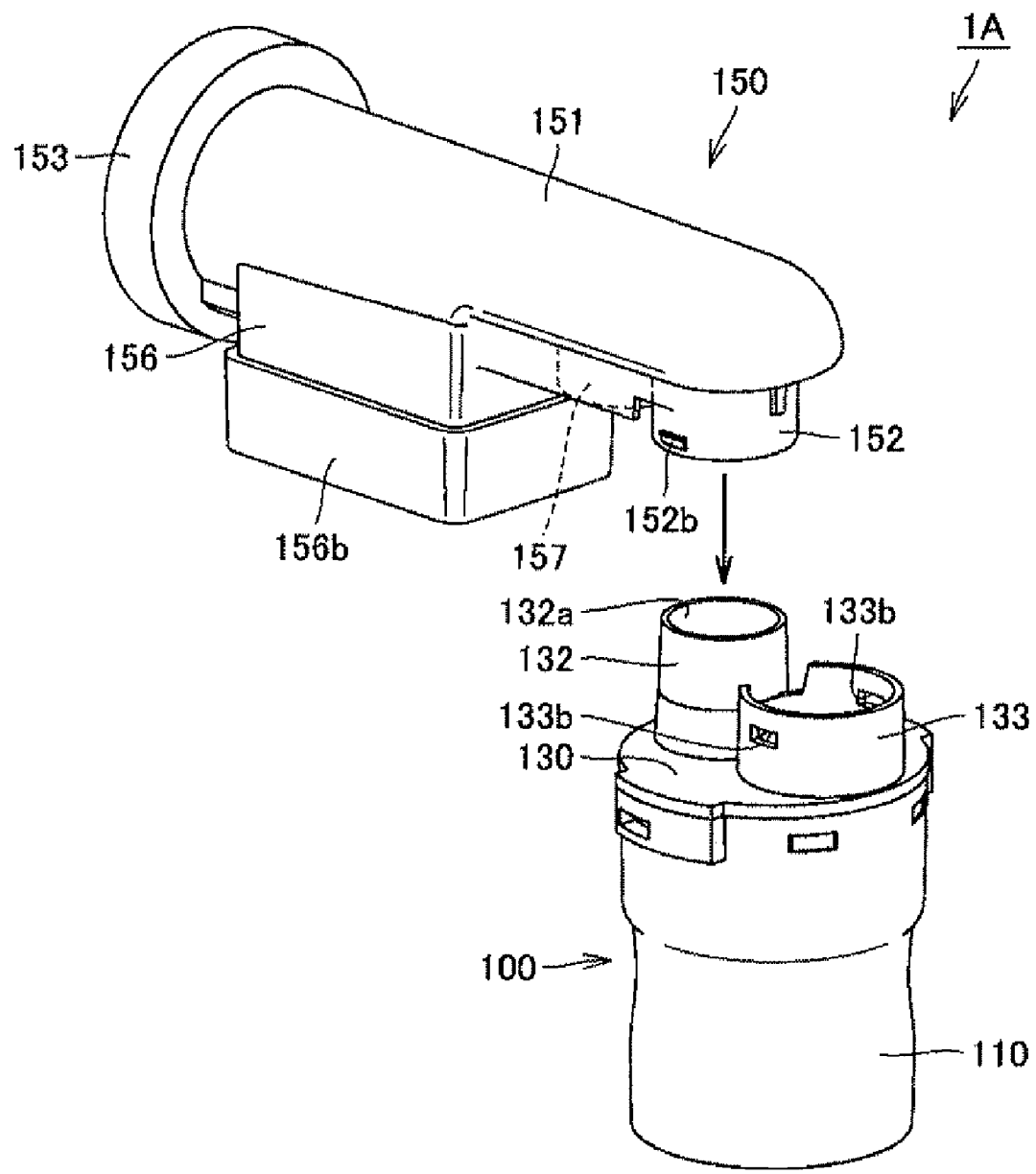
FIG. 5 is an exploded perspective view illustrating an assembly structure of the nebulizer body and the relay pipe in the usage state of the nebulizer of the first embodiment of the invention.
Figure 6:
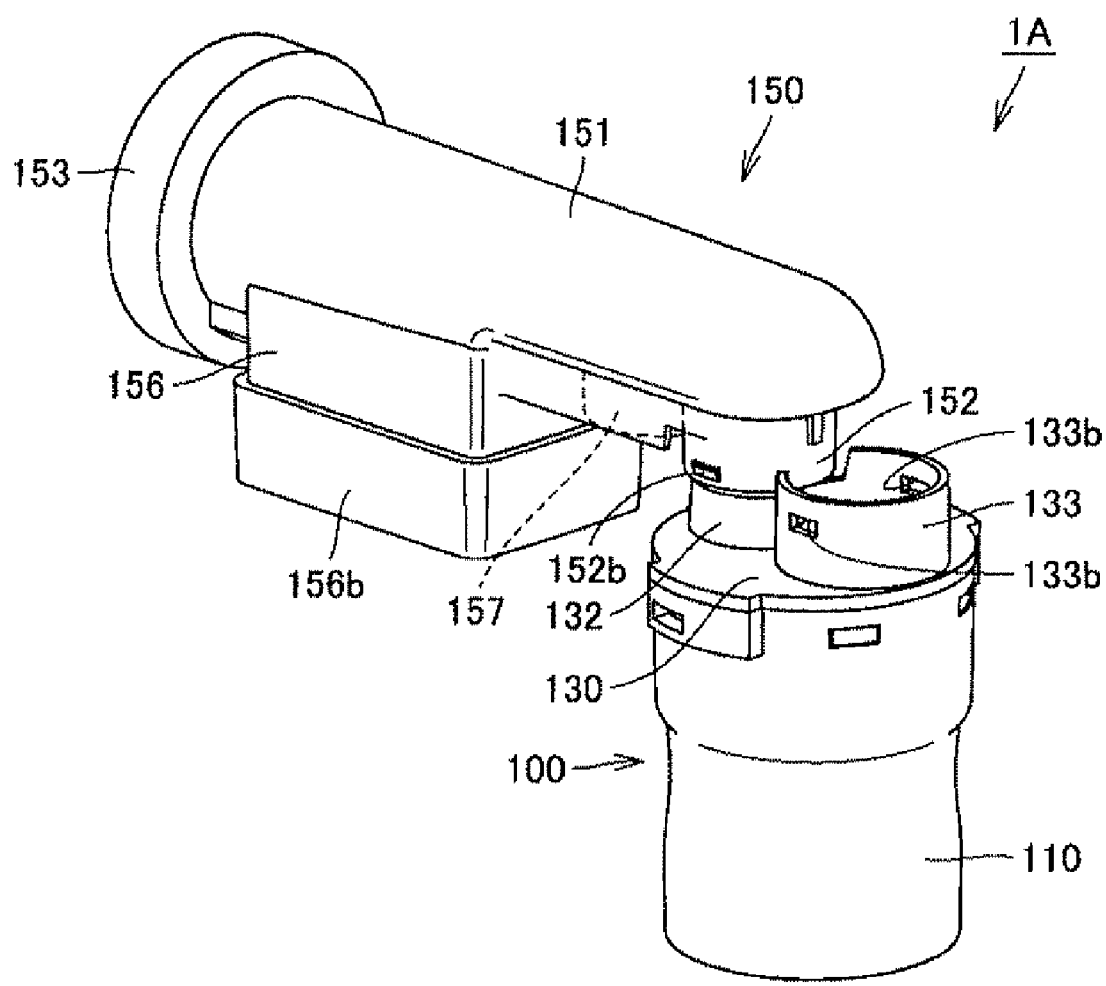
FIG. 6 is a perspective view of the nebulizer body and the relay pipe after assembly in the usage state of the nebulizer of the first embodiment of the invention.

FIG. 5 is an exploded perspective view illustrating an assembly structure of the nebulizer body and the relay pipe in the usage state, and FIG. 6 is a perspective view of the nebulizer body and the relay pipe after assembly in the usage state. A connection structure of the nebulizer body 100, the relay pipe 150, and the mask 160 in the usage state will be described with reference to FIGS. 3, 5, and 6.

As illustrated in FIG. 5, in the usage of the nebulizer 1A, the first connection portion 132 provided in the nebulizer body 100 is inserted in and connected to the fourth connection portion 152 provided in the relay pipe 150. At this point, the second connection portion 133 provided in the nebulizer body 100 is not covered with the relay pipe 150. The first connection portion 132 provided in the nebulizer body 100 and the fourth connection portion 152 provided in the relay pipe 150 are detachably connected, and the first connection portion 132 can be inserted in and removed from the fourth connection portion 152 as many times as needed.

Therefore, a connection structure between the nebulizer body 100 and the relay pipe 150 can be realized as illustrated in FIGS. 3 and 4. In order to actually use the nebulizer 1A, in addition to the connection between the nebulizer body 100 and the relay pipe 150, it is necessary that the tube 240 connected to the compressor 250 be connected to the third connection portion 114 provided in the nebulizer body 100, and it is necessary that the relay-pipe-side opening end 162 of the mask 160 be connected to the fifth connection portion 132 provided in the relay pipe 150.

An operation of the nebulizer 1A will be described with reference to FIG. 3. When the compressor 250 is activated, the air current is generated in the nebulizer body 100, the relay pipe 150, and the mask 160 as illustrated in FIG. 3.

Specifically, the compressed air is introduced into the nebulizer body 100 through the tube 240 and the compressed air introduction port 114a by the activation of the compressor 250. At this point, when the user performs the suction operation in order to inhale the aerosol, the space in the nebulizer body 100 becomes the negative pressure, and the valve body 142 bends to introduce the outer air from the outer air introduction port 101 into the nebulizer body 100.

The outer air taken in from the outer air introduction port 101 reaches the atomization portion through the introduction passage 102 formed in the suction pipe portion 134. In the atomization portion, the aerosol is produced by giving the atomized particles of the liquid 300 to the outer air including the outer air (compressed air) introduced from the compressed air introduction port 114a and the outer air taken in from the outer air introduction port 101. The produced aerosol reaches the aerosol lead-out port 132a provided in the nebulizer body 100 through the conveyance passage 103, and the aerosol flows in the conveyance passage 154a of the relay pipe 150 through the aerosol introduction port provided in the relay pipe 150. The aerosol flowing in the conveyance passage 154a of the relay pipe 150 is ejected to the space in the mask 160 through the aerosol ejection port 153a provided in the relay pipe 150. The aerosol ejected to the space in the mask 160 is inhaled in the body of the user from the mouth and/or nose of the user with the suction operation of the user.

During the inhalation of the aerosol, the exhaled air ejected from the mouth and/or nose of the user flows in the relay pipe 150 through the space in the mask 160. At this point, because a pressure in the discharge passage 154b is lower than a pressure in the conveyance passage 154a, the exhaled air flowing in the relay pipe 150 flows in the discharge passage 154b. The exhaled air flowing in the discharge passage 154b is discharged to the outside of the relay pipe 150 from the ejection portion 156 through the filter 156a.

Figure 7:
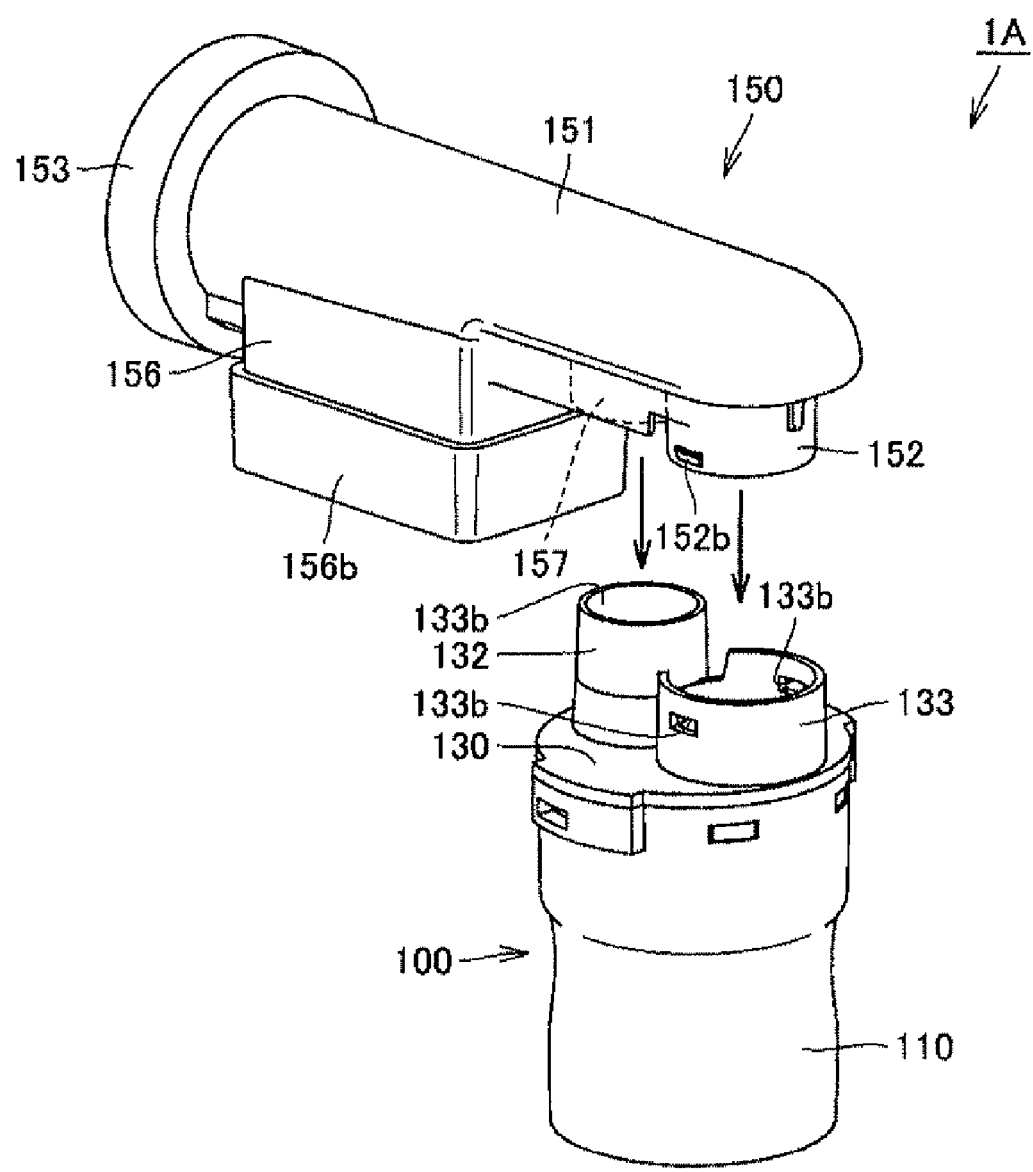
FIG. 7 is an exploded perspective view illustrating an assembly structure of the nebulizer body and the relay pipe in a disposal state of the nebulizer of the first embodiment of the invention.
Figure 8:
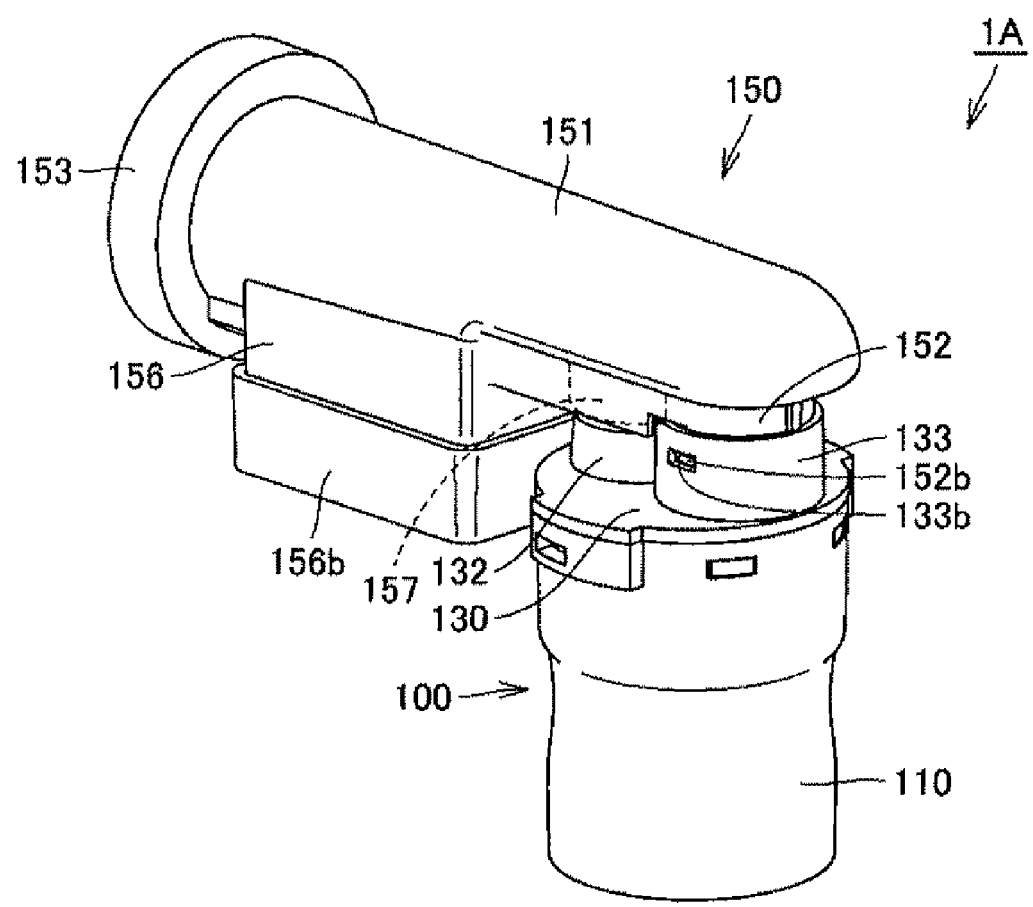
FIG. 8 is a perspective view of the nebulizer body and the relay pipe after assembly in the disposal state of the nebulizer of the first embodiment of the invention.
Figure 9:
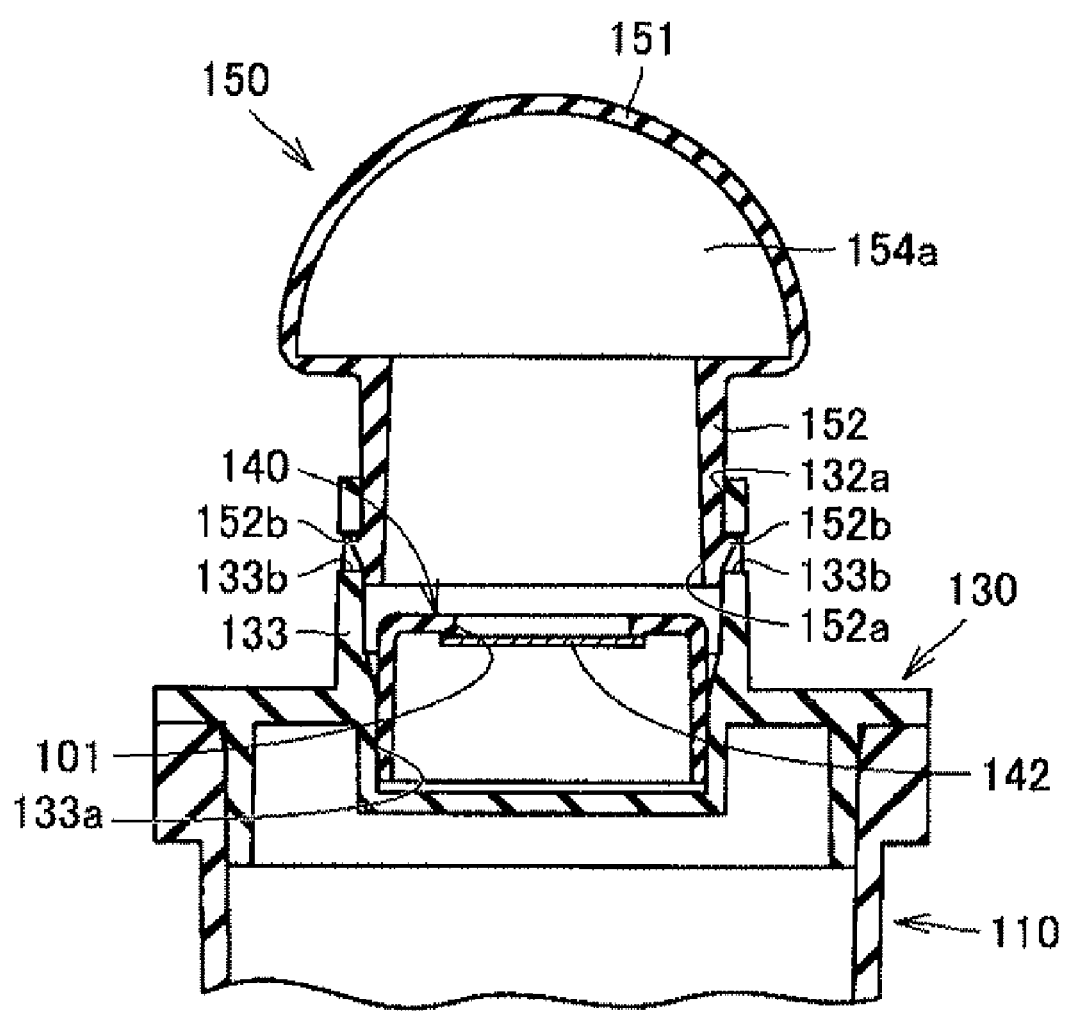
FIG. 9 is a longitudinal sectional view of the nebulizer body and the relay pipe after connection in the disposal state in which the nebulizer of the first embodiment of the invention.
Figure 10:
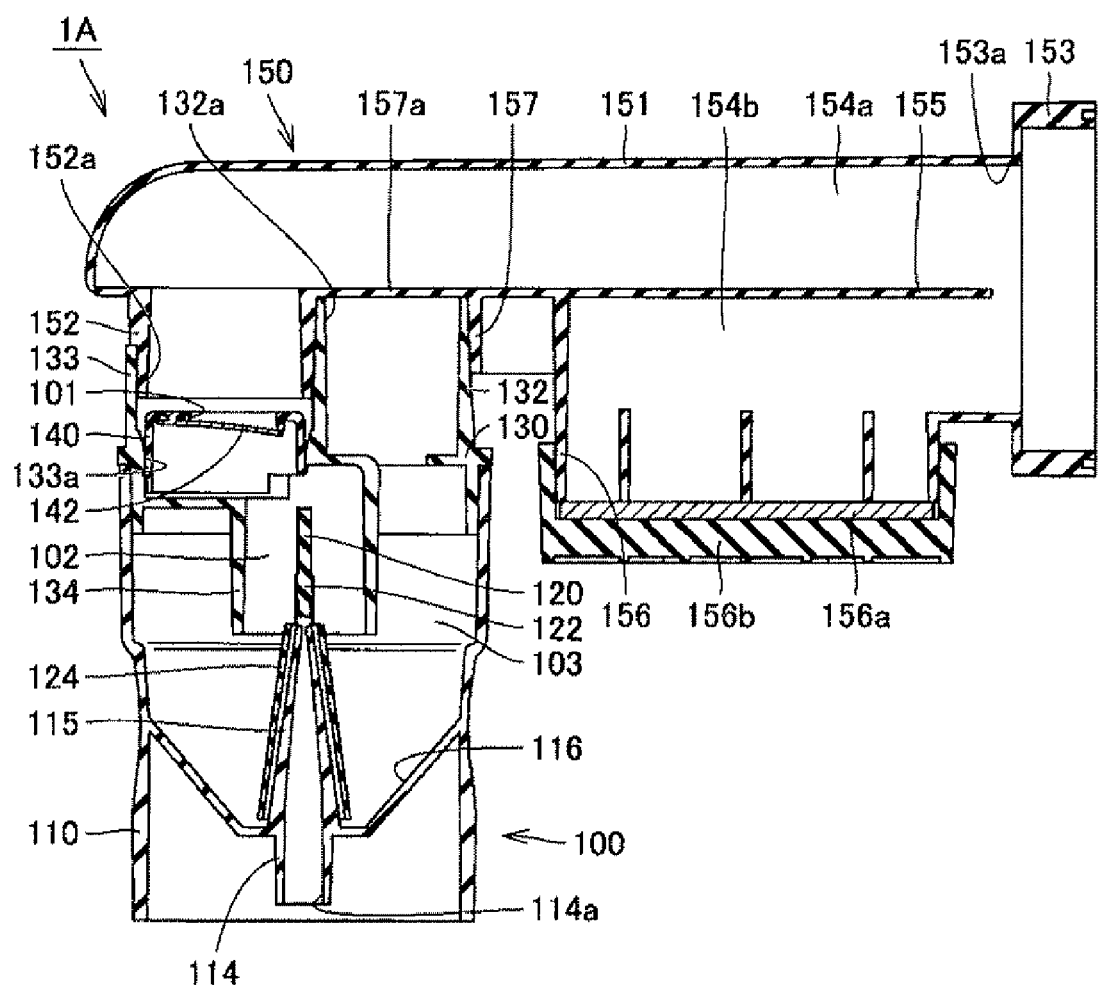
FIG. 10 is an enlarged sectional view illustrating a state in which a first connection portion and a fourth connection portion are connected after connection in the disposal state of the nebulizer of the first embodiment of the invention.

FIG. 7 is an exploded perspective view illustrating an assembly structure of the nebulizer body and the relay pipe in a disposal state, and FIG. 8 is a perspective view of the nebulizer body and the relay pipe after assembly in the disposal state. FIG. 9 is a longitudinal sectional view of the nebulizer body and the relay pipe after connection in the disposal state, and FIG. 10 is an enlarged sectional view illustrating a state in which the first connection portion and the fourth connection portion are connected after connection in the disposal state. A connection state of the nebulizer body 100 and the relay pipe 150 in the disposal state will be described with reference to FIGS. 7 to 10.

As illustrated in FIG. 7, in the disposal, the fourth connection portion 152 provided in the relay pipe 150 is inserted in and connected to the second connection portion 133 provided in the nebulizer body 100, and the first connection portion 132 provided in the nebulizer body 100 is concurrently inserted in and connected to the sixth connection portion 157 provided in the relay pipe 150. Therefore, the connection structure between the nebulizer body 100 and the relay pipe 150 is realized as illustrated in FIGS. 8 and 9.

At this point, as illustrated in FIG. 9, in the nebulizer body 100 and relay pipe 150 which are connected in the disposal state, the aerosol lead-out port 132a provided in the nebulizer body 100 is blocked by the blocking portion 157a provided in the relay pipe 150. Accordingly, the nebulizer body 100 and the relay pipe 150 cannot be used in the disposal state.

The fourth connection portion 152 provided in the relay pipe 150 and the second connection portion 133 provided in the nebulizer body 100 are connected by the so-called fixed fitting in which the fourth connection portion 152 and the second connection portion 133 cannot substantially be released once are assembled. Specifically, as illustrated in FIG. 10, the latching projection 152b provided in the circumferential surface of the fourth connection portion 152 is latched in the latching hole portion 133b made in the circumferential surface of the second connection portion 133, thereby connecting the fourth connection portion 152 provided in the relay pipe 150 and the second connection portion 133 provided in the nebulizer body 100. More particularly, part of the latching projection 152b acts as the hook-like latching pawl portion, part of the latching hole portion 133b acts as the latching step portion, and the latching pawl portion is fitted in the latching step portion. Therefore, the fitting cannot be released, and the fixed fitting is realized in the latching between the latching projection 152b and the latching hole portion 133b.

Once the nebulizer 1A becomes the disposal state as illustrated in FIGS. 8 and 9, because the state in which the aerosol lead-out port 132a is blocked cannot substantially be released, the nebulizer body 100 and the relay pipe 150 cannot be reused after the usage.

Thus, the nebulizer 1A of the first embodiment is configured such that the nebulizer body 100 and the relay pipe 150 take the usage state that is of the first connection state in which the relay pipe 150 is detachably connected to the nebulizer body 100 and the disposal state that is of the second connection state in which the relay pipe 150 is connected to the nebulizer body 100 while being not able to be detached from the nebulizer body 100. In the usage state that is of the first state, the aerosol lead-out port 132a provided in the nebulizer body 100 and the aerosol introduction port 152a provided in the relay pipe 150 are configured to be communicated with each other. In the disposal state that is of the second state, the aerosol lead-out port 132a provided in the nebulizer body 100 is configured to be blocked by the blocking portion 157a provided in the relay pipe 150. Accordingly, in the nebulizer 1A of the first embodiment, the adoption of the configurations can prohibit the reuse of the nebulizer body 100 and relay pipe 150 after the usage by the simple manipulation, and the generation of the health problem such as the secondary infection can be prevented before happens.

Second Embodiment

Figure 11:
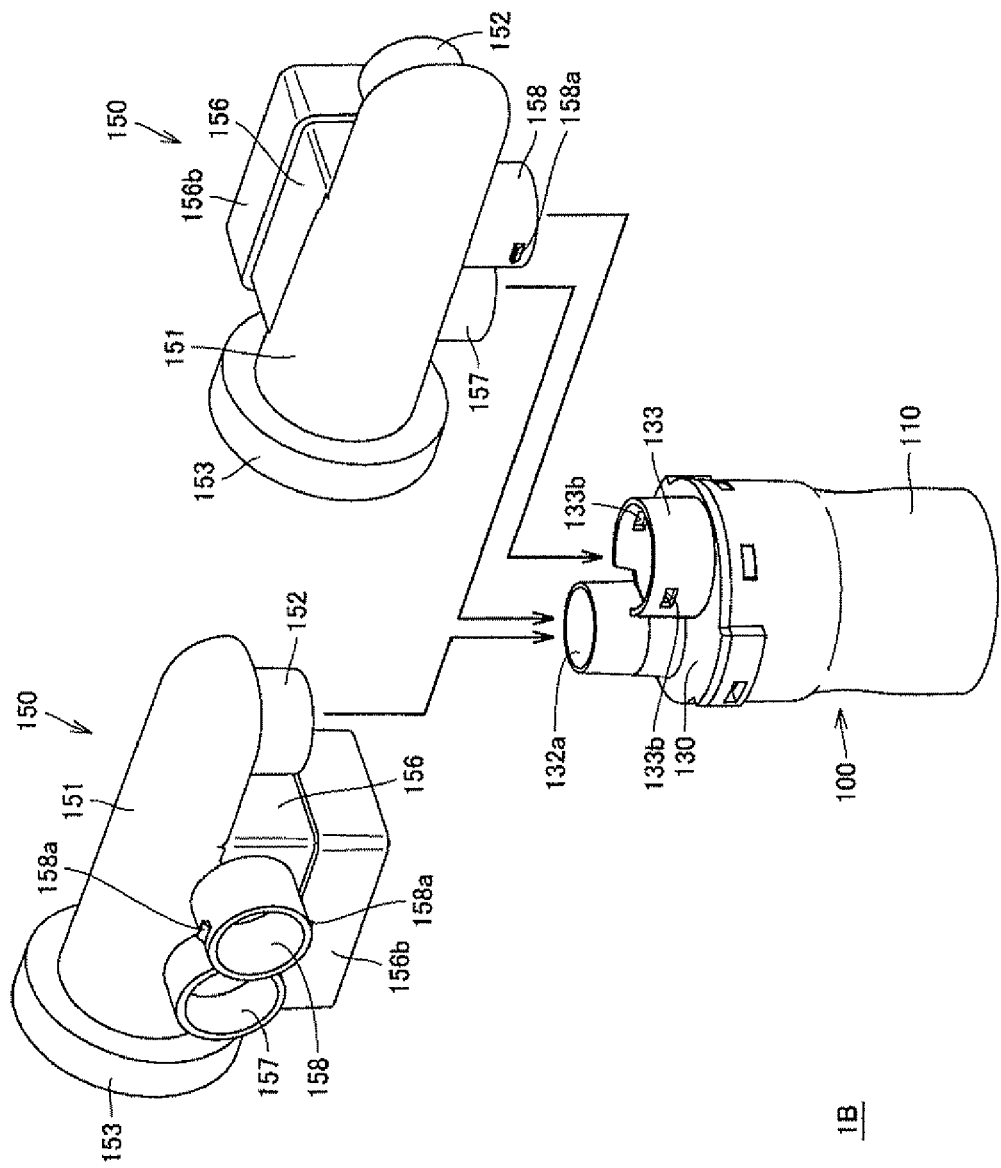
FIG. 11 is an exploded perspective view illustrating an assembly structure of a nebulizer body and a relay pipe in a usage state and a disposal state of a nebulizer according to a second embodiment of the invention.
Figure 12:
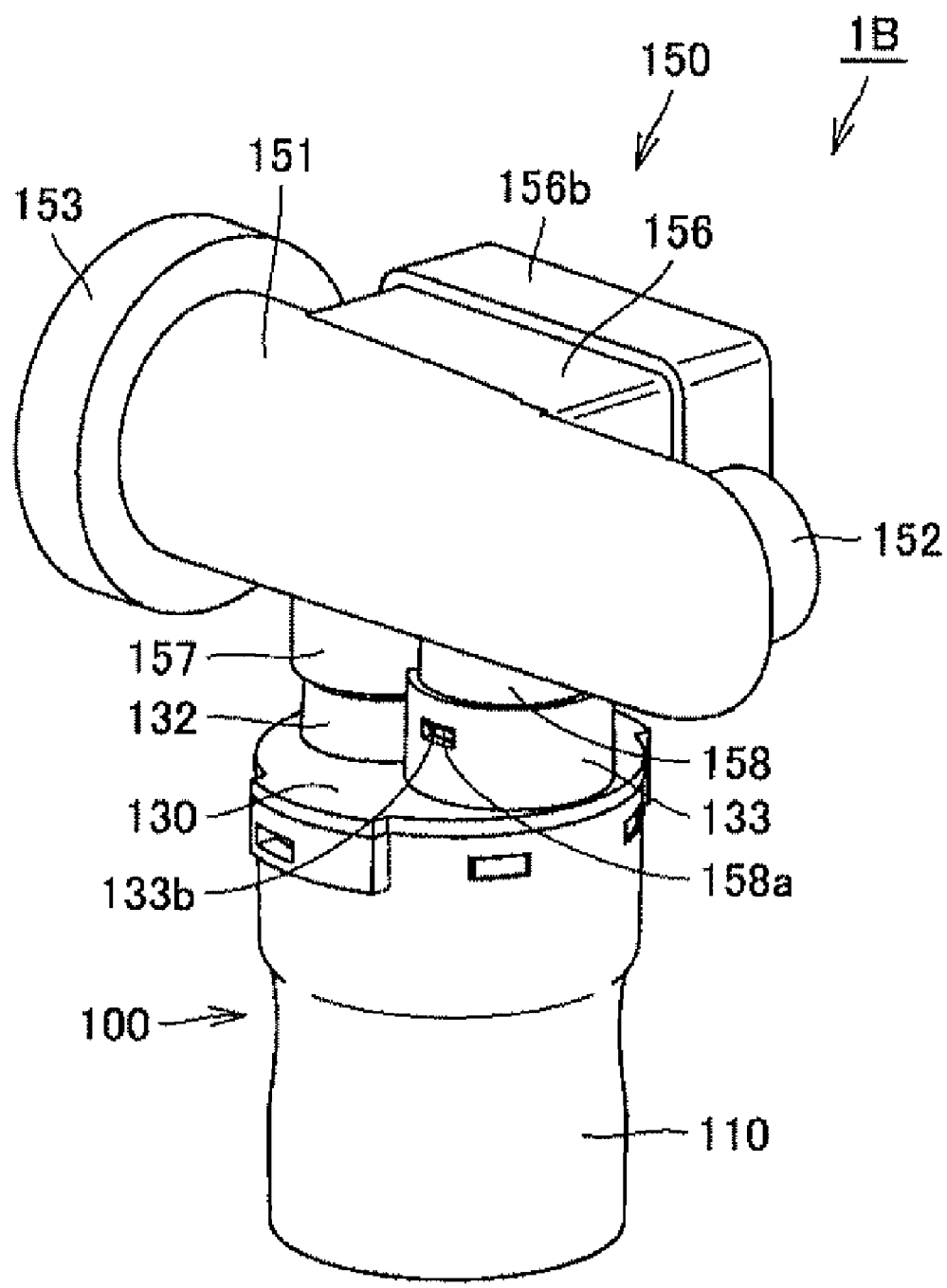
FIG. 12 is a perspective view of the nebulizer body and the relay pipe after assembly in the disposal state of the nebulizer of the second embodiment of the invention.

FIG. 11 is an exploded perspective view illustrating an assembly structure of a nebulizer body and a relay pipe in a usage state and a disposal state of a nebulizer according to a second embodiment of the invention, and FIG. 12 is a perspective view of the nebulizer body and the relay pipe after assembly in the disposal state. In FIGS. 11 and 12, the component similar to that of the nebulizer 1A of the first embodiment is designated by the same symbol, and the description is not repeated.

As illustrated in FIG. 11, a nebulizer 1B of the second embodiment differs from the nebulizer 1A of the first embodiment in the structure of the relay pipe 150. Specifically, in the configuration of the nebulizer 1A of the first embodiment, the sixth connection portion 157 is provided in the lower surface of the relay pipe 150. On the other hand, in the nebulizer 1B of the second embodiment, the sixth connection portion 157 is laterally projected from the side surface of the relay pipe 150. A sidewall of the relay pipe in the portion surrounded by the sixth connection portion 157 acts as the blocking portion.

In the nebulizer 1B of the second embodiment, a seventh connection portion 158 is laterally projected from the side surface of the relay pipe 150 in addition to the sixth connection portion 157. The seventh connection portion 158 is a region that is connected to the first connection portion 132 provided in the nebulizer body 100 in the disposal state, and a latching projection 158a is provided in the circumferential surface of the seventh connection portion 158.

In the nebulizer 1B of the second embodiment, in the disposal, the seventh connection portion 158 provided in the relay pipe 150 is inserted in and connected to the second connection portion 133 provided in the nebulizer body 100, and the first connection portion 132 provided in the nebulizer body 100 is concurrently inserted in and connected to the sixth connection portion 157 provided in the relay pipe 150. Therefore, the connection structure between the nebulizer body 100 and the relay pipe 150 is realized as illustrated in FIG. 12. In the connection state, the aerosol lead-out port 132a provided in the nebulizer body 100 is blocked by the blocking portion that is formed in a predetermined region of the sidewall of the relay pipe 150, and the fourth connection portion 152 provided in the relay pipe 150 and the second connection portion 133 provided in the nebulizer body 100 are connected by the so-called fixed fitting in which the fourth connection portion 152 and the second connection portion 133 cannot substantially be released once are connected.

Once the nebulizer 1B becomes the disposal state as illustrated in FIG. 12, because the state in which the aerosol lead-out port 132a is blocked cannot substantially be released, the nebulizer body 100 and relay pipe 150 cannot be reused after the usage. Accordingly, in the nebulizer 1B of the second embodiment, the adoption of the configurations can prohibit the reuse of the nebulizer body 100 and relay pipe 150 after the usage by the simple manipulation, and the generation of the health problem such as the secondary infection can be prevented before happens.

Third Embodiment

Figure 13:
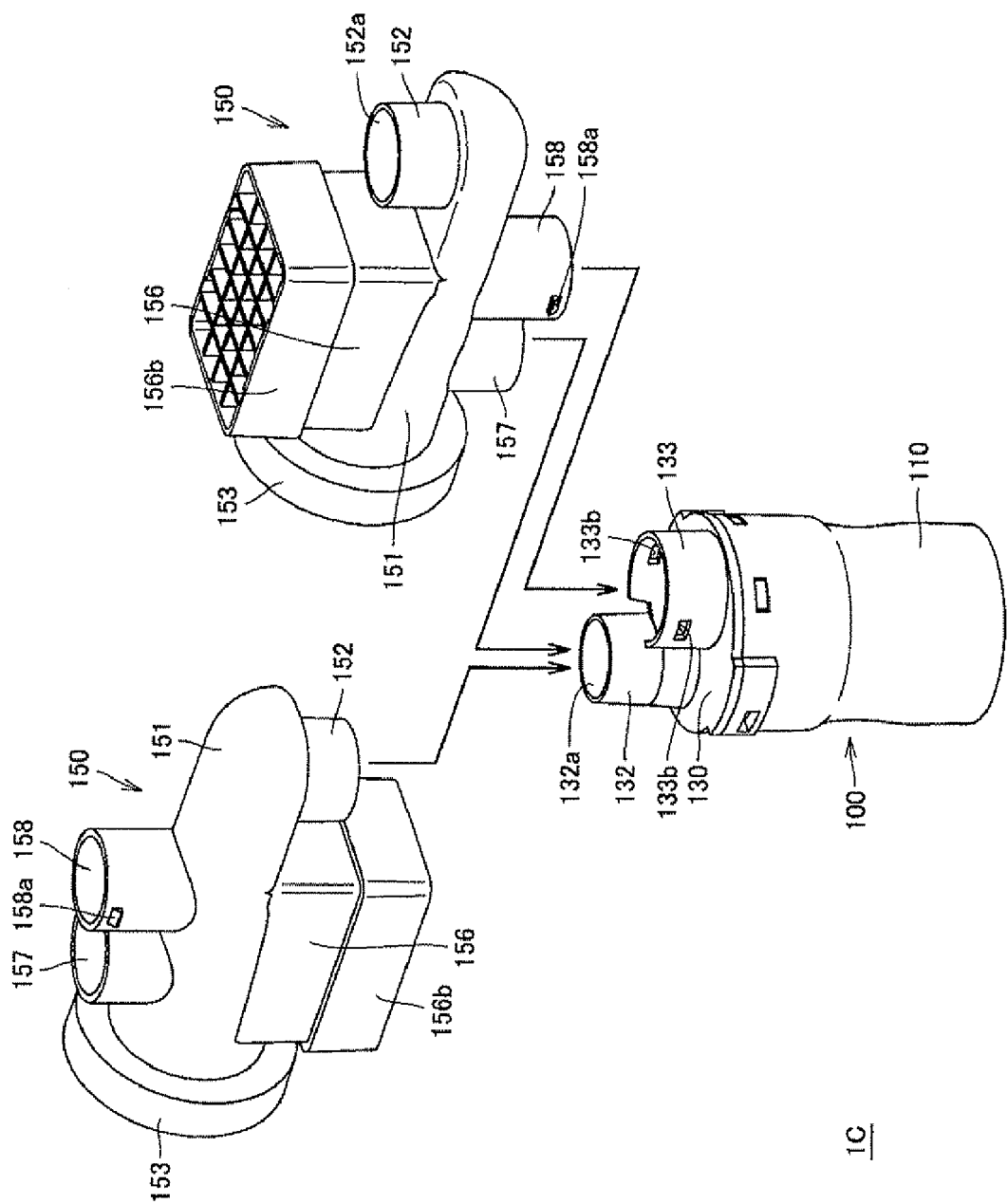
FIG. 13 is an exploded perspective view illustrating an assembly structure of a nebulizer body and a relay pipe in a usage state and a disposal state of a nebulizer according to a third embodiment of the invention.
Figure 14:
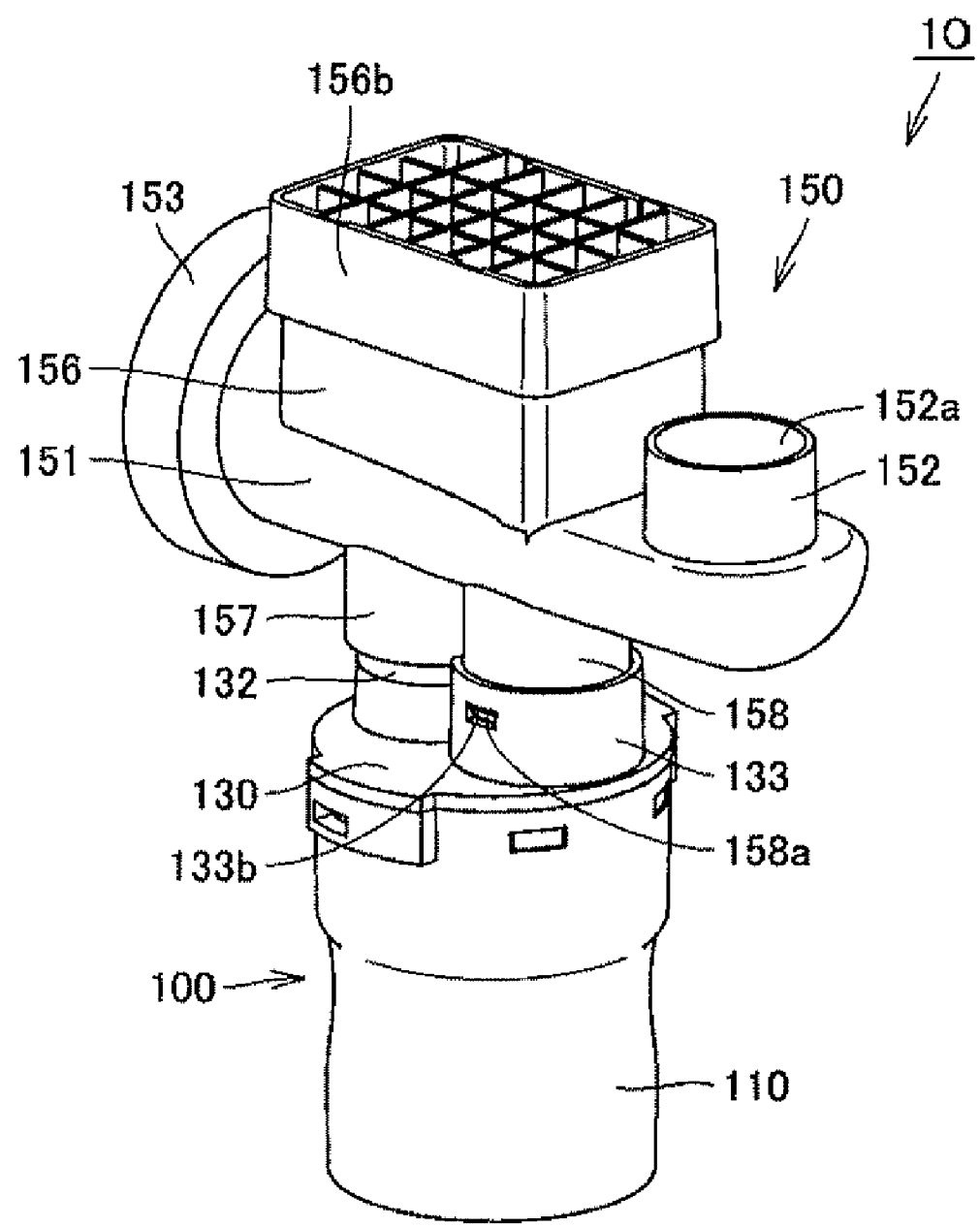
FIG. 14 is a perspective view of the nebulizer body and the relay pipe after assembly in the disposal state of the nebulizer of the third embodiment of the invention.

FIG. 13 is an exploded perspective view illustrating an assembly structure of a nebulizer body and a relay pipe in a usage state and a disposal state of a nebulizer according to a third embodiment of the invention, and FIG. 14 is a perspective view of the nebulizer body and the relay pipe after assembly in the disposal state. In FIG. 14, the component similar to that of the nebulizer 1C of the second embodiment is designated by the same symbol, and the description is not repeated.

As illustrated in FIG. 13, a nebulizer 1C of the third embodiment differs from the nebulizer 1B of the second embodiment in the structure of the relay pipe 150. Specifically, in the configuration of the nebulizer 1B of the second embodiment, the sixth connection portion 157 and the seventh connection portion 158 are provided in the side surface of the relay pipe 150. On the other hand, in the nebulizer 1C of the third embodiment, the sixth connection portion 157 and the seventh connection portion 158 are projected upward from the upper surface of the relay pipe 150. An upper wall of the relay pipe in the portion surrounded by the sixth connection portion 157 acts as the blocking portion. Similarly to the first embodiment of the invention, the latching projection 158a is provided in the circumferential surface of the seventh connection portion 158.

In the nebulizer 1C of the third embodiment, in the disposal, the seventh connection portion 158 provided in the relay pipe 150 is inserted in and connected to the second connection portion 133 provided in the nebulizer body 100, and the first connection portion 132 provided in the nebulizer body 100 is concurrently inserted in and connected to the sixth connection portion 157 provided in the relay pipe 150. Therefore, the connection structure between the nebulizer body 100 and the relay pipe 150 is realized as illustrated in FIG. 14. In the connection state, the aerosol lead-out port 132a provided in the nebulizer body 100 is blocked by the blocking portion that is formed in a predetermined region of the sidewall of the relay pipe 150, and the fourth connection portion 152 provided in the relay pipe 150 and the second connection portion 133 provided in the nebulizer body 100 are connected by the so-called fixed fitting in which the fourth connection portion 152 and the second connection portion 133 cannot substantially be released once are connected.

Once the nebulizer 1C becomes the disposal state as illustrated in FIG. 14, because the state in which the aerosol lead-out port 132a is blocked cannot substantially be released, the nebulizer body 100 and relay pipe 150 cannot be reused after the usage. Accordingly, in the nebulizer 1C of the third embodiment, the adoption of the configurations can prohibit the reuse of the nebulizer body 100 and relay pipe 150 after the usage by the simple manipulation, and the generation of the health problem such as the secondary infection can be prevented before happens.

Fourth Embodiment

Figure 15:
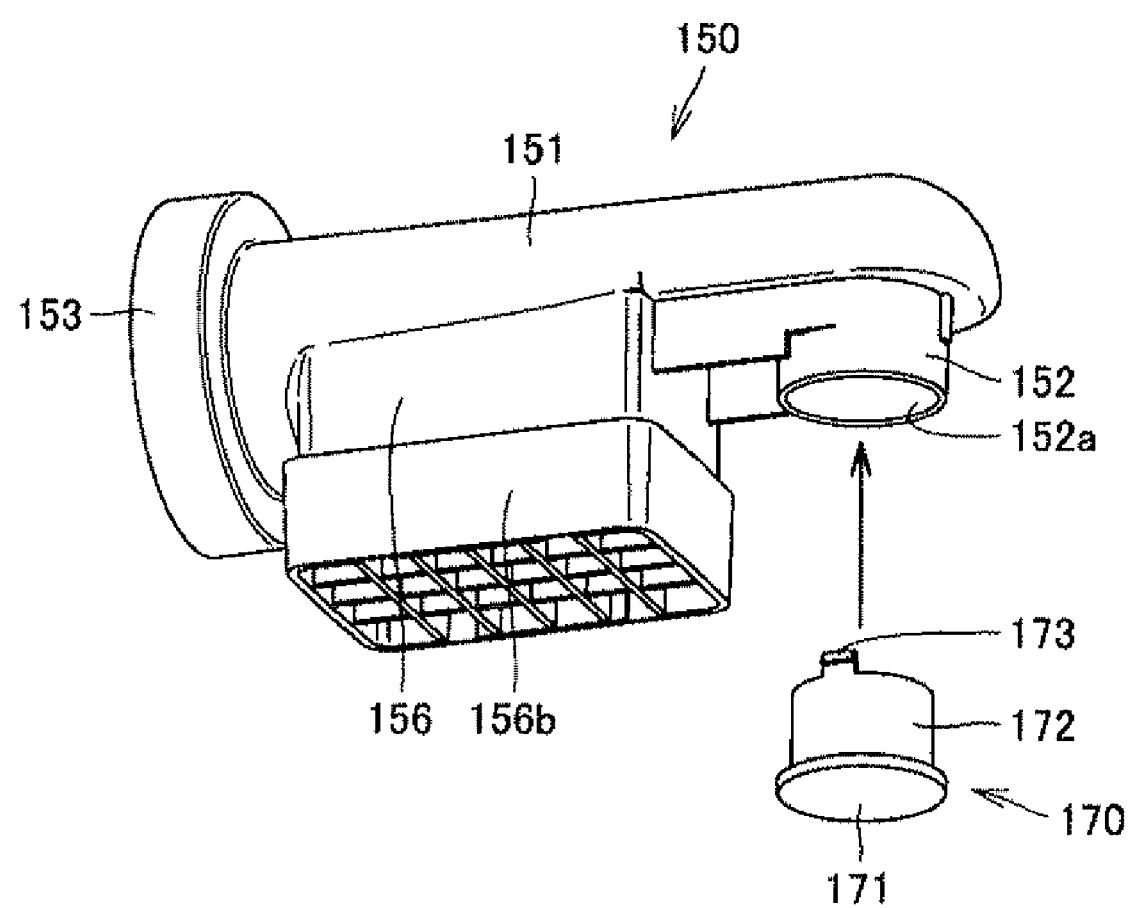
FIG. 15 is an exploded perspective view illustrating an assembly structure of a relay pipe and a blocking member in a disposal state of a nebulizer according to a fourth embodiment of the invention.
Figure 16:
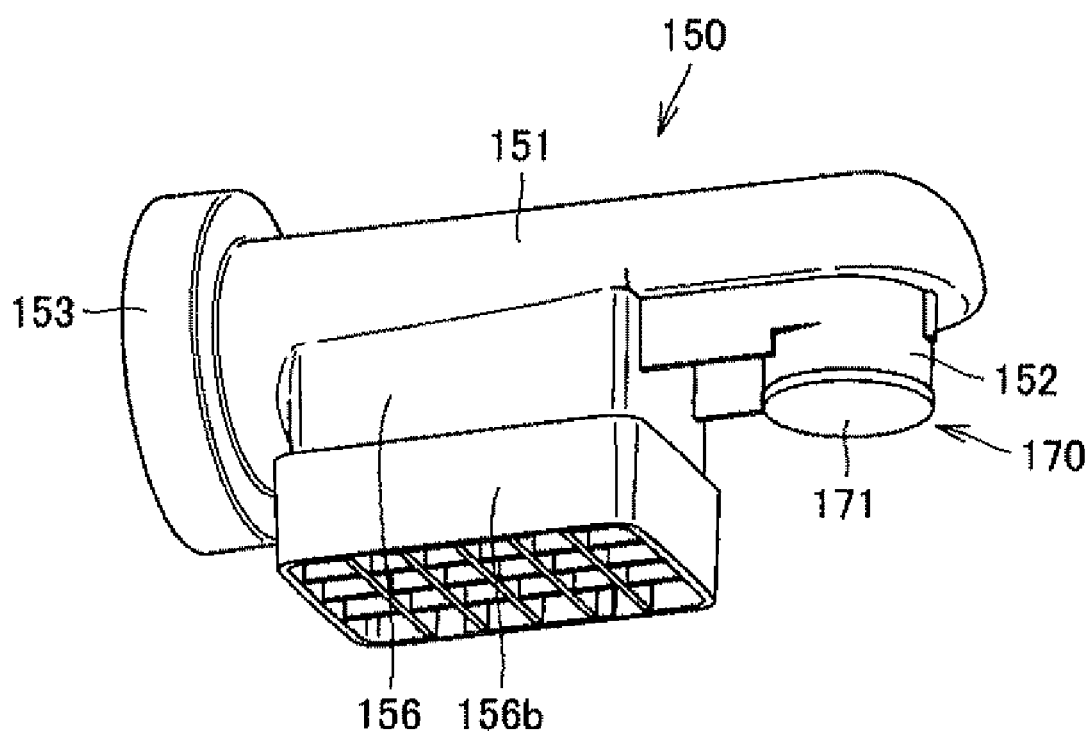
FIG. 16 is a perspective view of the relay pipe and the blocking member after assembly in the disposal state of the nebulizer of the fourth embodiment of the invention.
Figure 17:
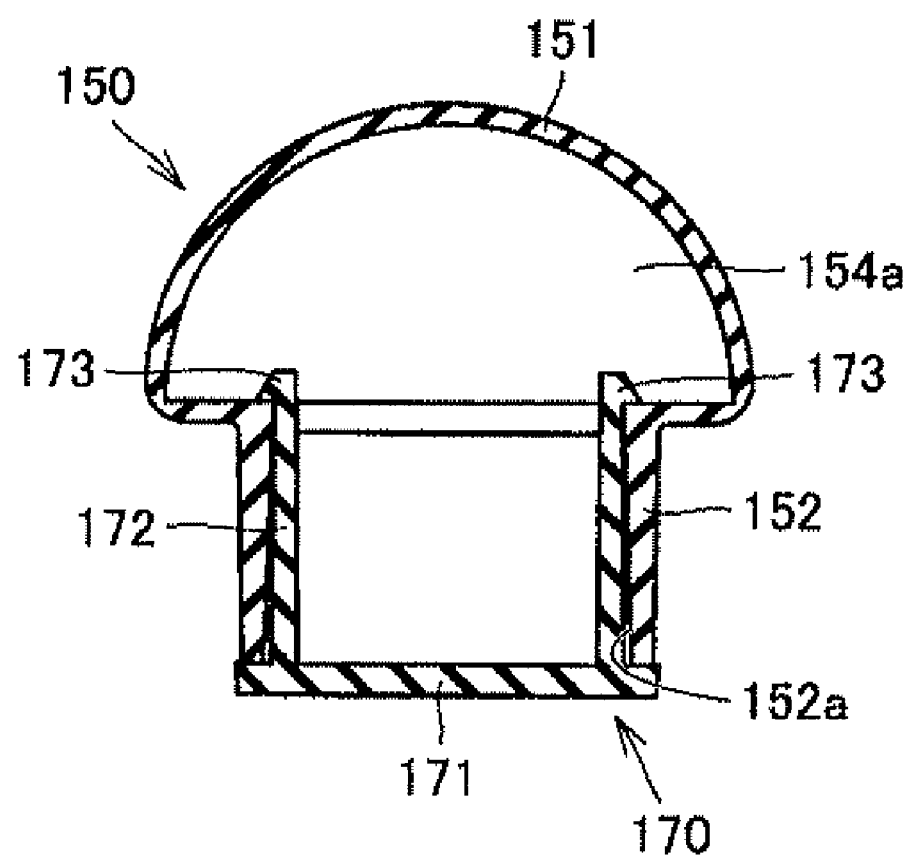
FIG. 17 is an enlarged sectional view illustrating a state in which a fourth connection portion and the blocking member are connected after connection in the disposal state of the nebulizer of the fourth embodiment of the invention.

FIG. 15 is an exploded perspective view illustrating an assembly structure of a relay pipe and a blocking member in a disposal state of a nebulizer according to a fourth embodiment of the invention, and FIG. 16 is a perspective view of the relay pipe and the blocking member after assembly in the disposal state. FIG. 17 is an enlarged sectional view illustrating a state in which a fourth connection portion and the blocking member are connected after connection in the disposal state of the nebulizer of the fourth embodiment. In FIGS. 15 to 17, the component similar to that of the nebulizer 1A of the first embodiment is designated by the same symbol, and the description is not repeated.

As illustrated in FIG. 15, the nebulizer of the fourth embodiment differs slightly from the nebulizer 1A of the first embodiment in the structure of the relay pipe 150. Specifically, the relay pipe 150 of the nebulizer of the fourth embodiment includes neither the sixth connection portion 157 that is provided in the relay pipe 150 of the nebulizer 1A of the first embodiment nor the latching projection 152b that is provided in the circumferential surface of the fourth connection portion 152. The nebulizer of the fourth embodiment includes a cap-shaped blocking member 170 that is independently provided as another component while separated from the nebulizer body and the relay pipe 150. The blocking member 170 includes a cover portion 171 that is of the blocking portion, a cylindrical wall portion 172 that is vertically provided from the cover portion 171, and a latching projection 173 that is of the pair of latching pawl portions provided at the leading end of the cylindrical wall portion 172. The blocking member 170 is produced by injection molding using a resin material and the like.

In the nebulizer of the fourth embodiment, in the disposal, the blocking member 170 is inserted in and connected to the fourth connection portion 152 provided in the relay pipe 150. Therefore, the connection structure between the relay pipe 150 and the blocking member 170 is realized as illustrated in FIG. 16.

At this point, as illustrated in FIG. 16, in the relay pipe 150 and blocking member 170 which are connected in the disposal state, the aerosol introduction port 152a provided in the relay pipe 150 is blocked by the cover portion 171 of the blocking member 170. Accordingly, the relay pipe 150 cannot be used in the disposal state.

The fourth connection portion 152 and blocking member 170 which are provided in the relay pipe 150 are connected by the so-called fixed fitting in which the fourth connection portion 152 and the blocking member 170 cannot substantially be released once are connected. Specifically, as illustrated in FIG. 17, the latching projection 152b provided at the leading end of the cylindrical wall portion 172 of the blocking member 170 is latched in the lower wall of the cylindrical portion 151 of the relay pipe 150, thereby connecting the fourth connection portion 152 provided in the relay pipe 150 and the blocking member 170. More particularly, part of the latching projection 173 acts as the hook-like latching pawl portion, a boundary portion between the lower wall of the cylindrical portion 151 and the fourth connection portion 152 acts as the latching step portion, and the latching pawl portion is fitted in the latching step portion. Therefore, the fitting cannot be released, and the fixed fitting is realized in the latching between the latching projection 173 and the lower wall of the cylindrical portion 151.

Once the nebulizer becomes the disposal state as illustrated in FIG. 16, because the state in which the aerosol introduction port 152a is blocked cannot substantially be released, the relay pipe 150 cannot be reused after the usage. Accordingly, in the nebulizer of the fourth embodiment, the adoption of the configurations can prohibit the reuse of the relay pipe 150 after the usage by the simple manipulation, and the generation of the health problem such as the secondary infection can be prevented before happens.

Figure 18:
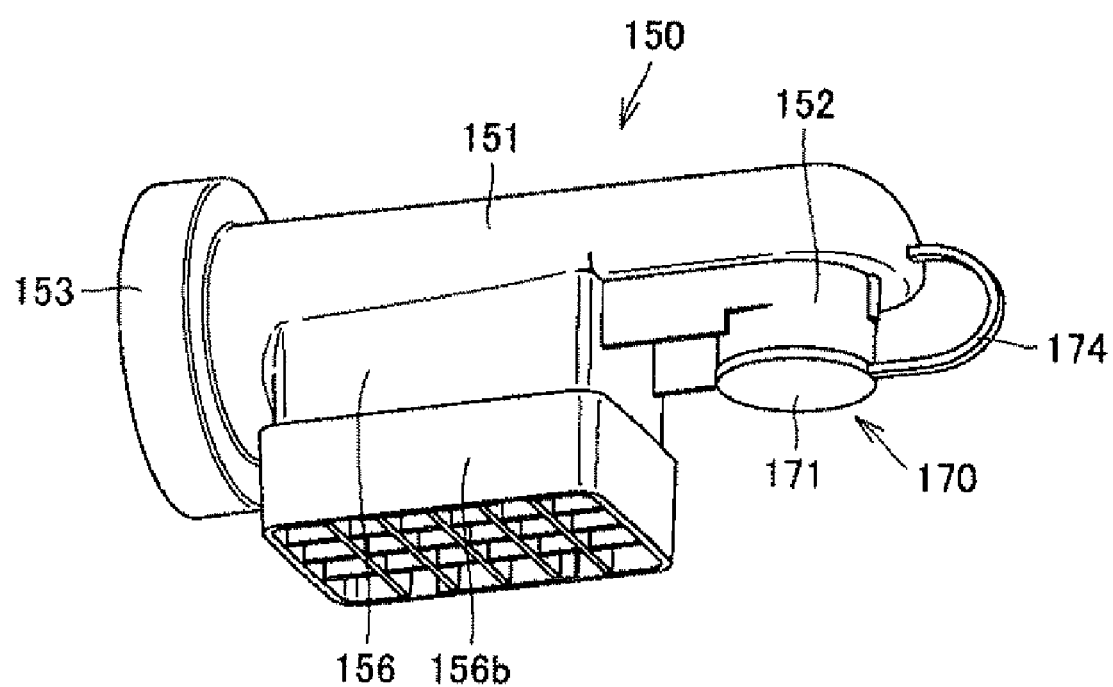
FIG. 18 is a perspective view of a relay pipe after assembly in a disposal state of a nebulizer according to a first modification of the fourth embodiment of the invention.
Figure 19:
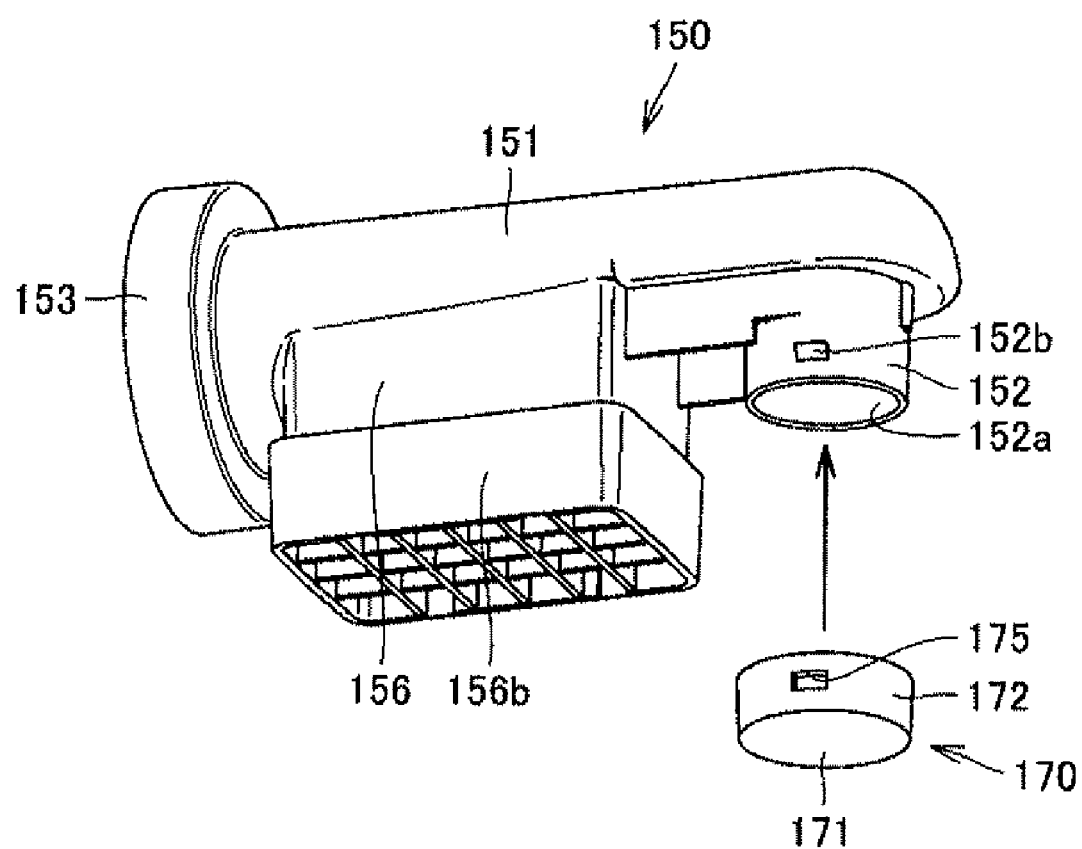
FIG. 19 is an exploded perspective view for describing an assembly structure in a disposal state of a relay pipe and a blocking member of a nebulizer according to a second modification of the fourth embodiment of the invention.

FIG. 18 is a perspective view of a relay pipe after assembly in a disposal state for the purpose of description of a first modification of the nebulizer of the fourth embodiment, and FIG. 19 is an exploded perspective view for describing an assembly structure in a disposal state of a relay pipe and a blocking member of a second modification of the nebulizer of the fourth embodiment.

In the first modification illustrated in FIG. 18, the relay pipe 150 and blocking member 170 of the fourth embodiment are integrally formed. Specifically, a deformable coupling portion 174 that is extended in a thin rod shape is projected from the rear end of the relay pipe 150, and the blocking member 170 is formed at the leading end of the coupling portion 174. For the configuration of the first modification, advantageously the problem with the loss of the blocking member 170 in advance of the disposal can be prevented before happened in addition to the effect of the fourth embodiment.

In the second modification illustrated in FIG. 19, the latching step portion provided in the relay pipe 150 of the fourth embodiment is formed by a pair of latching hole portions 175 provided in the cylindrical wall portion 172 of the blocking member 170, and the latching projection 173 that is of the pair of latching pawl portions provided in the blocking member 170 of the fourth embodiment is formed by the pair of latching projections 152b provided in the circumferential surface of the fourth connection portion 152 of the relay pipe 150. The effect similar to that of the fourth embodiment can be obtained in the configuration of the second modification.

Fifth Embodiment

Figure 20:
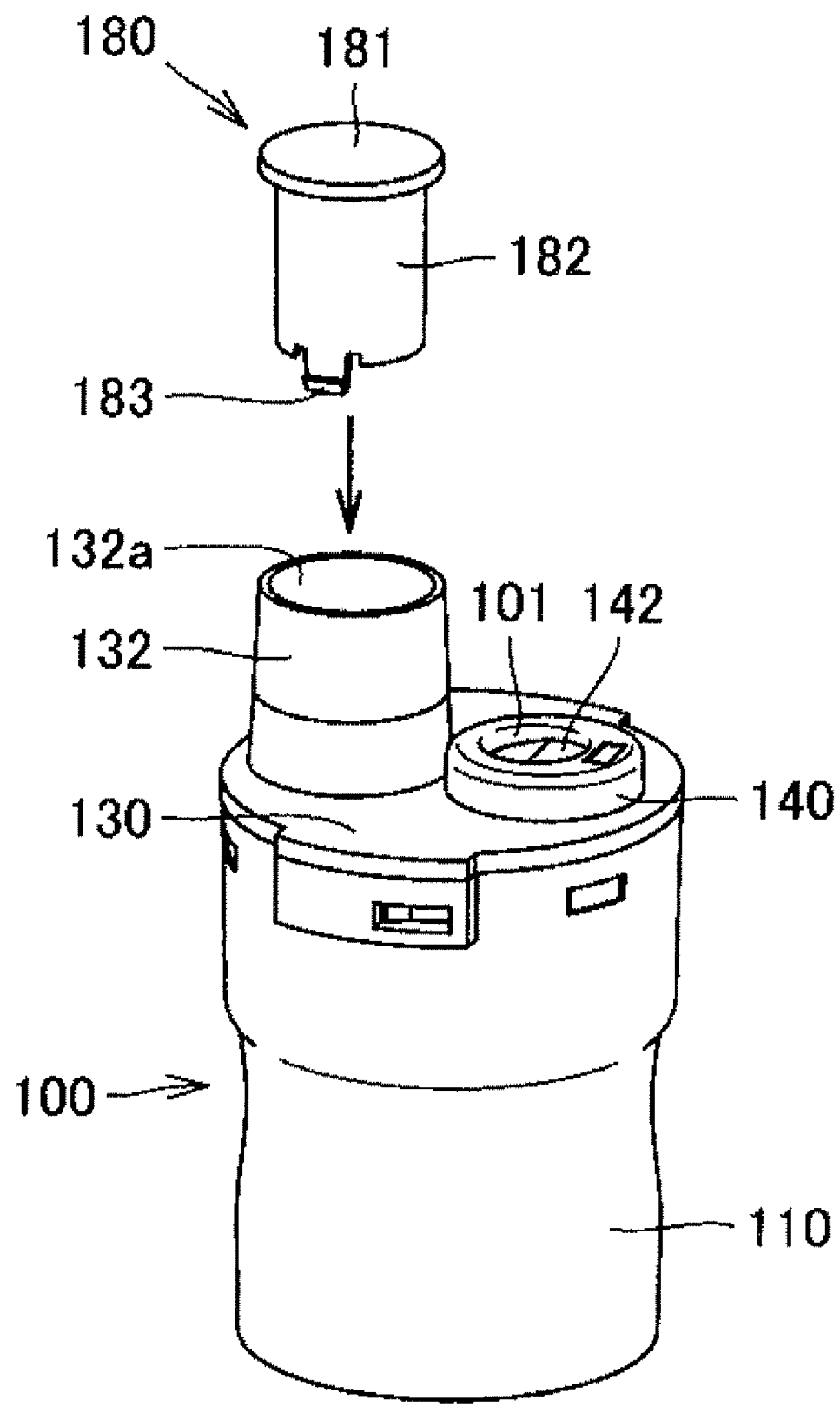
FIG. 20 is an exploded perspective view illustrating an assembly structure of a nebulizer body and a blocking member in a disposal state of a nebulizer according to a fifth embodiment of the invention.
Figure 21:
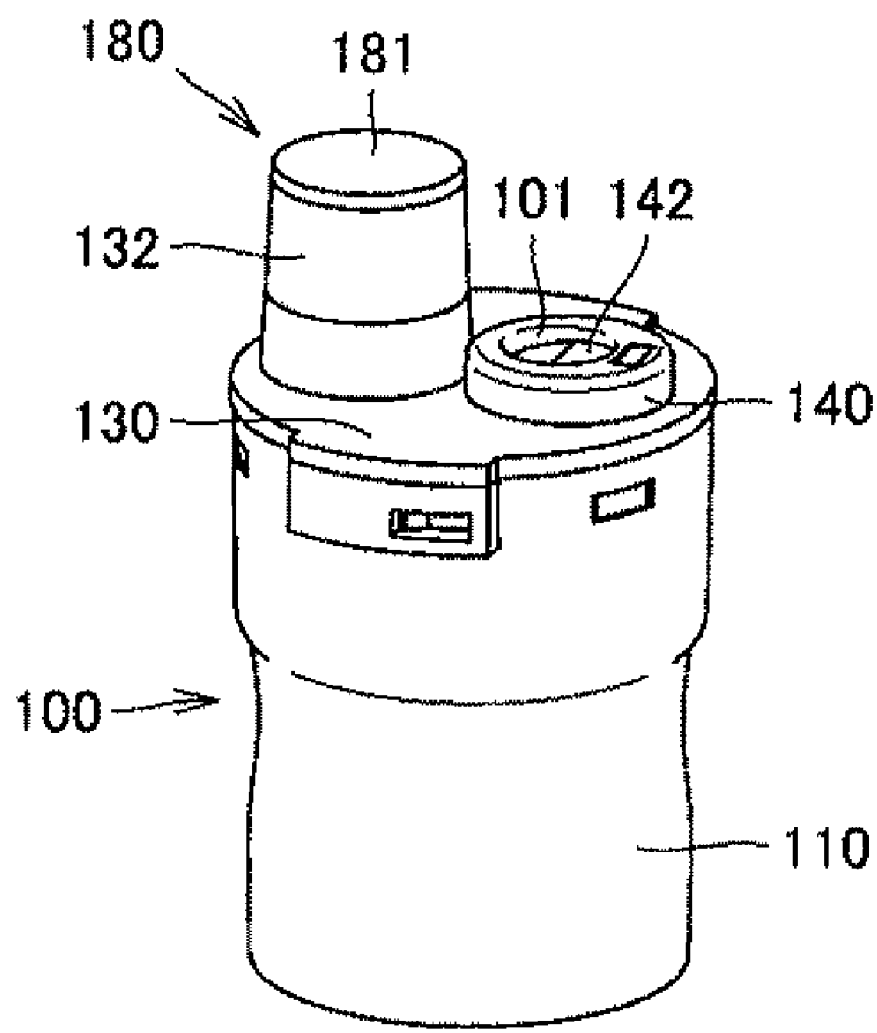
FIG. 21 is a perspective view of a nebulizer body and a blocking member after assembly in the disposal state of the nebulizer of the fifth embodiment of the invention.
Figure 22:
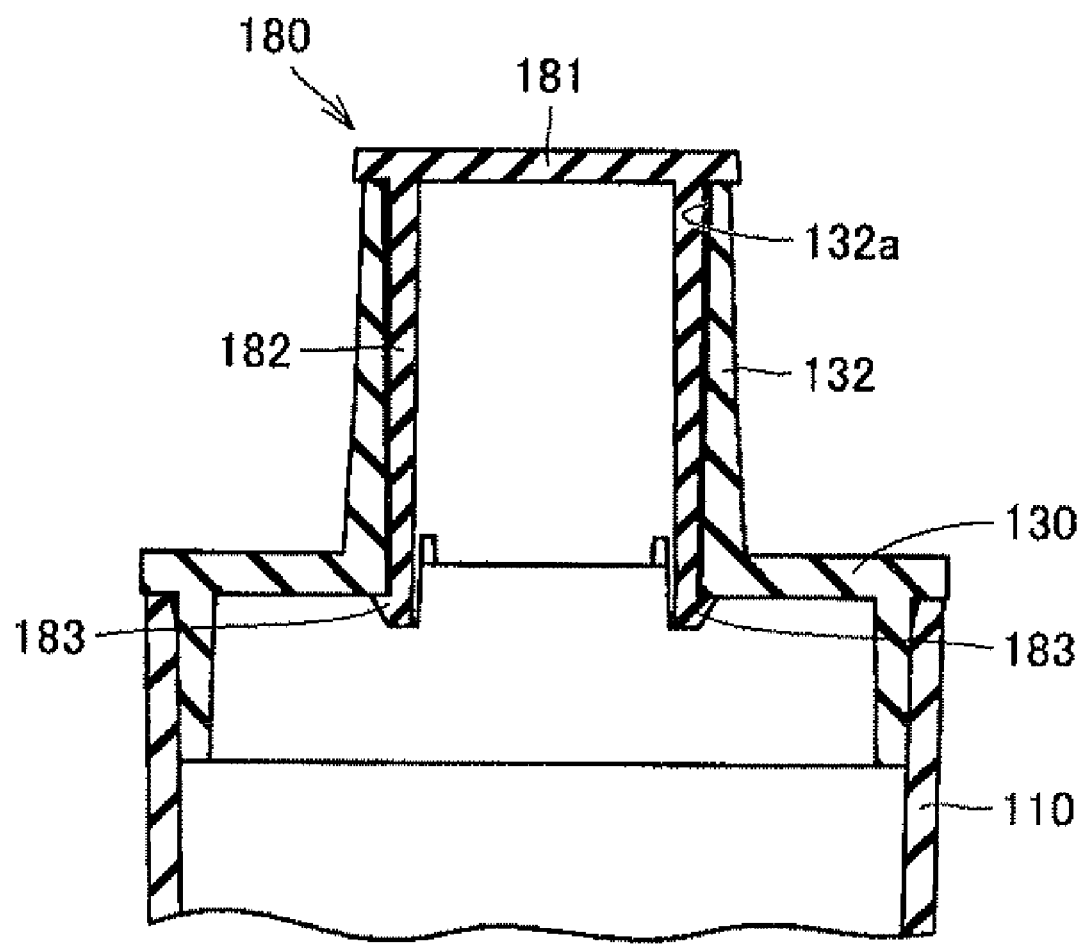
FIG. 22 is an enlarged sectional view illustrating a connection state of a first connection portion and the blocking member after connection in the disposal state of the nebulizer of the fifth embodiment of the invention.

FIG. 20 is an exploded perspective view illustrating an assembly structure of a nebulizer body and a relay pipe in a disposal state of a nebulizer according to a fifth embodiment of the invention, and FIG. 21 is a perspective view of a nebulizer body and a blocking member after assembly in the disposal state. FIG. 22 is an enlarged sectional view illustrating a connection state of a first connection portion and the blocking member after connection in the disposal state of the nebulizer of the fifth embodiment. In FIGS. 20 to 22, the component similar to that of the nebulizer 1A of the first embodiment is designated by the same symbol, and the description is not repeated.

As illustrated in FIG. 20, the nebulizer of the fifth embodiment differs slightly from the nebulizer 1A of the first embodiment in the structure of the nebulizer body 100. Specifically, the nebulizer body 100 of the nebulizer of the fifth embodiment does not include the second connection portion 133 that is provided in the nebulizer body 100 of the nebulizer 1A of the first embodiment, and therefore the nebulizer body 100 does not include the latching hole portion 133b that is made in the circumferential surface of the second connection portion 133. The nebulizer of the fifth embodiment includes a cap-shaped blocking member 180 that is independently provided as another component while separated from the nebulizer body 100 and the relay pipe. The blocking member 180 includes a cover portion 181 that is of the blocking portion, a cylindrical wall portion 182 that is vertically provided from the cover portion 181, and a latching projection 183 that is of the pair of latching pawl portions provided at the leading end of the cylindrical wall portion 182. The blocking member 180 is produced by injection molding using a resin material and the like.

In the nebulizer of the fifth embodiment, in the disposal, the blocking member 180 is inserted in and connected to the first connection portion 132 provided in the nebulizer body 100. Therefore, the connection structure between the nebulizer body 100 and the blocking member 180 is realized as illustrated in FIG. 21.

At this point, as illustrated in FIG. 21, in nebulizer body 100 and blocking member 180 which are connected in the disposal state, the aerosol lead-out port 132a provided in the nebulizer body 100 is blocked by the cover portion 181 of the blocking member 180. Accordingly, the nebulizer body 100 cannot be used in the disposal state.

The first connection portion 132 and blocking member 180 which are provided in the nebulizer body 100 are connected by the so-called fixed fitting in which the first connection portion 132 and the blocking member 180 cannot substantially be released once are connected. Specifically, as illustrated in FIG. 22, the latching projection 183 provided at the leading end of the cylindrical wall portion 182 of the blocking member 180 is latched in the lower surface of the flow passage forming body 130 of the nebulizer body 100, thereby connecting the first connection portion 132 and blocking member 180 which are provided in the nebulizer body 100. More particularly, part of the latching projection 183 acts as the hook-like latching pawl portion, the boundary portion between the lower surface of the flow passage forming body 130 and the first connection portion 132 acts as the latching step portion, and the latching pawl portion is fitted in the latching step portion. Therefore, the fitting cannot be released, and the fixed fitting is realized in the latching between the latching projection 183 and the lower surface of the flow passage forming body 130.

Once the nebulizer becomes the disposal state as illustrated in FIG. 21, because the state in which the aerosol lead-out port 132a is blocked cannot substantially be released, the nebulizer body 100 cannot be reused after the usage. Accordingly, in the nebulizer of the fifth embodiment, the adoption of the configurations can prohibit the reuse of the nebulizer body 100 after the usage by the simple manipulation, and the generation of the health problem such as the secondary infection can be prevented before happens.

Figure 23:
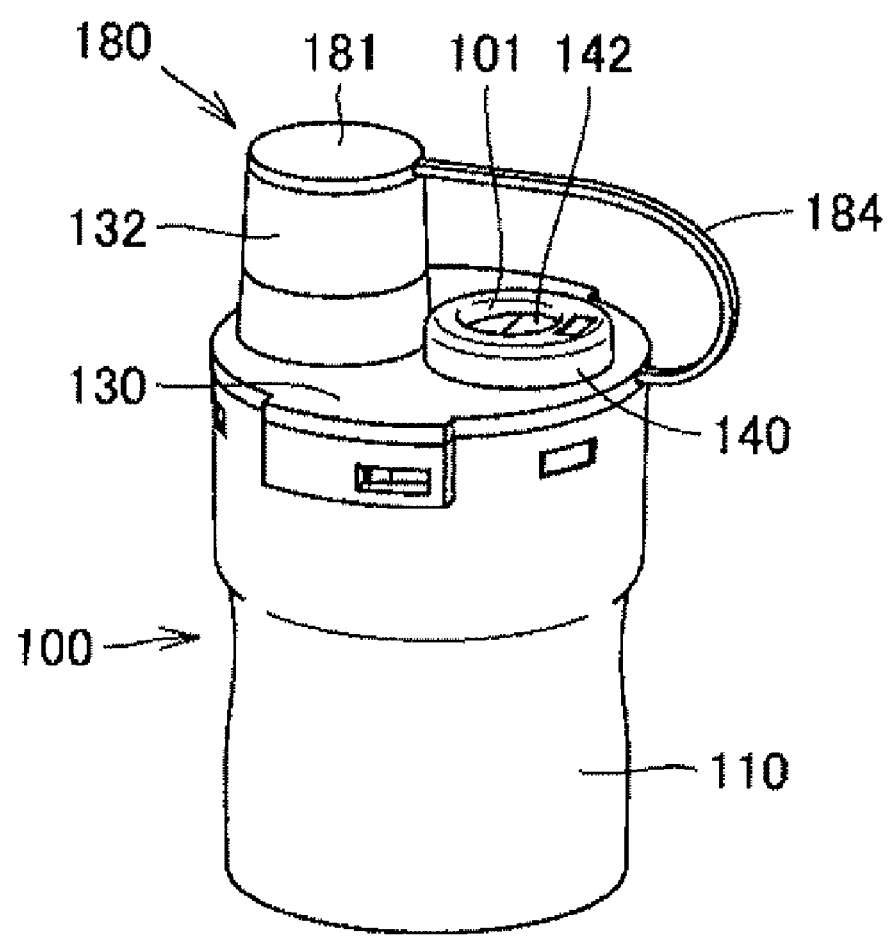
FIG. 23 is a perspective view of a nebulizer body after assembly in a disposal state of a nebulizer according to a first modification of the fifth embodiment of the invention.
Figure 24:
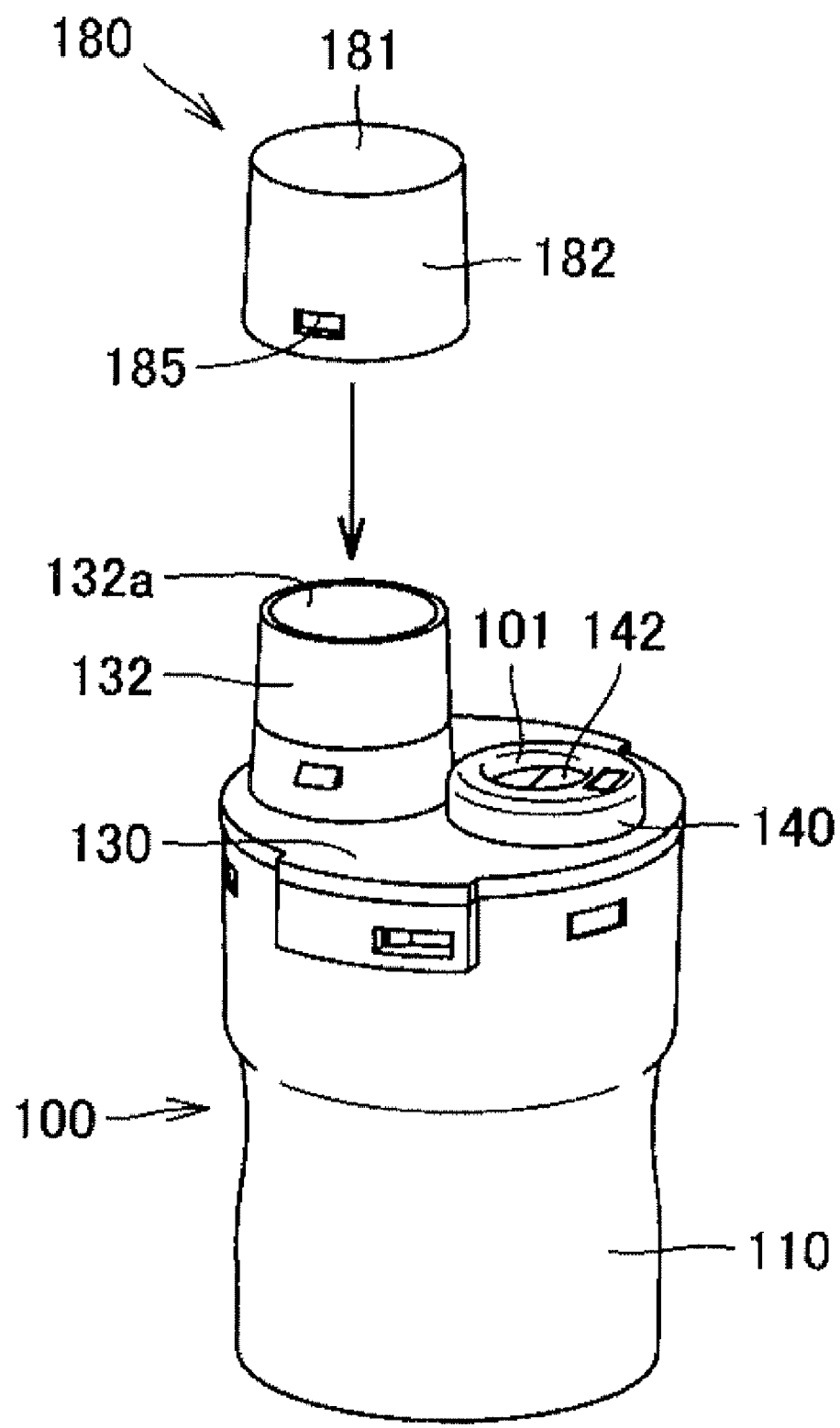
FIG. 24 is an exploded perspective view for describing an assembly structure in a disposal state of a nebulizer body and a blocking member of a nebulizer according to a second modification of the fifth embodiment of the invention.

FIG. 23 is a perspective view of a nebulizer body after assembly in a disposal state of a nebulizer according to a first modification of the fifth embodiment, and FIG. 24 is an exploded perspective view of an assembly structure in a disposal state of a nebulizer body and a blocking member for the purpose of description of a second modification of the nebulizer of the fifth embodiment.

In the first modification illustrated in FIG. 23, the nebulizer body 100 and blocking member 180 of the fifth embodiment are integrally formed. Specifically, a deformable coupling portion 184 that is extended in a thin rod shape is projected from the circumferential surface of the flow passage forming body 130 of the nebulizer body 100, and the blocking member 180 is formed at the leading end of the coupling portion 184. For the configuration of the first modification, advantageously the problem with the loss of the blocking member 180 in advance of the disposal can be prevented before happened in addition to the effect of the fifth embodiment.

In the second modification illustrated in FIG. 24, the latching step portion provided in the nebulizer body 100 of the fifth embodiment is formed by a pair of latching hole portions 185 provided in the cylindrical wall portion 182 of the blocking member 180, and the latching projection 183 that is of the pair of latching pawl portions provided in the blocking member 180 of the fifth embodiment is formed by the pair of latching projections 132b provided in the circumferential surface of the first connection portion 132 of the nebulizer body 100. The effect similar to that of the fifth embodiment can be obtained in the configuration of the second modification.

Sixth Embodiment

Figure 25:
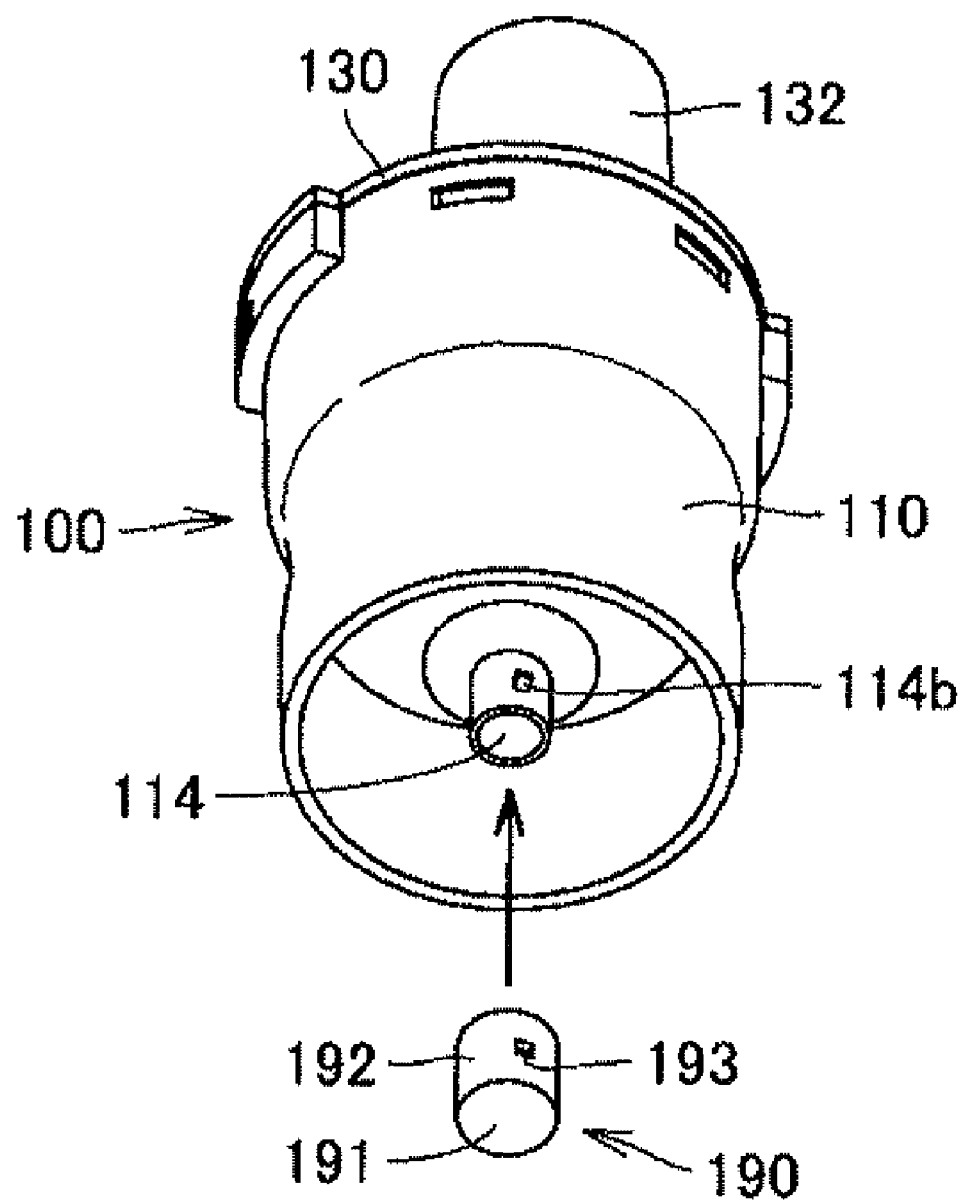
FIG. 25 is an exploded perspective view illustrating an assembly structure of a nebulizer body and a blocking member in a disposal state of a nebulizer according to a sixth embodiment of the invention.
Figure 26:
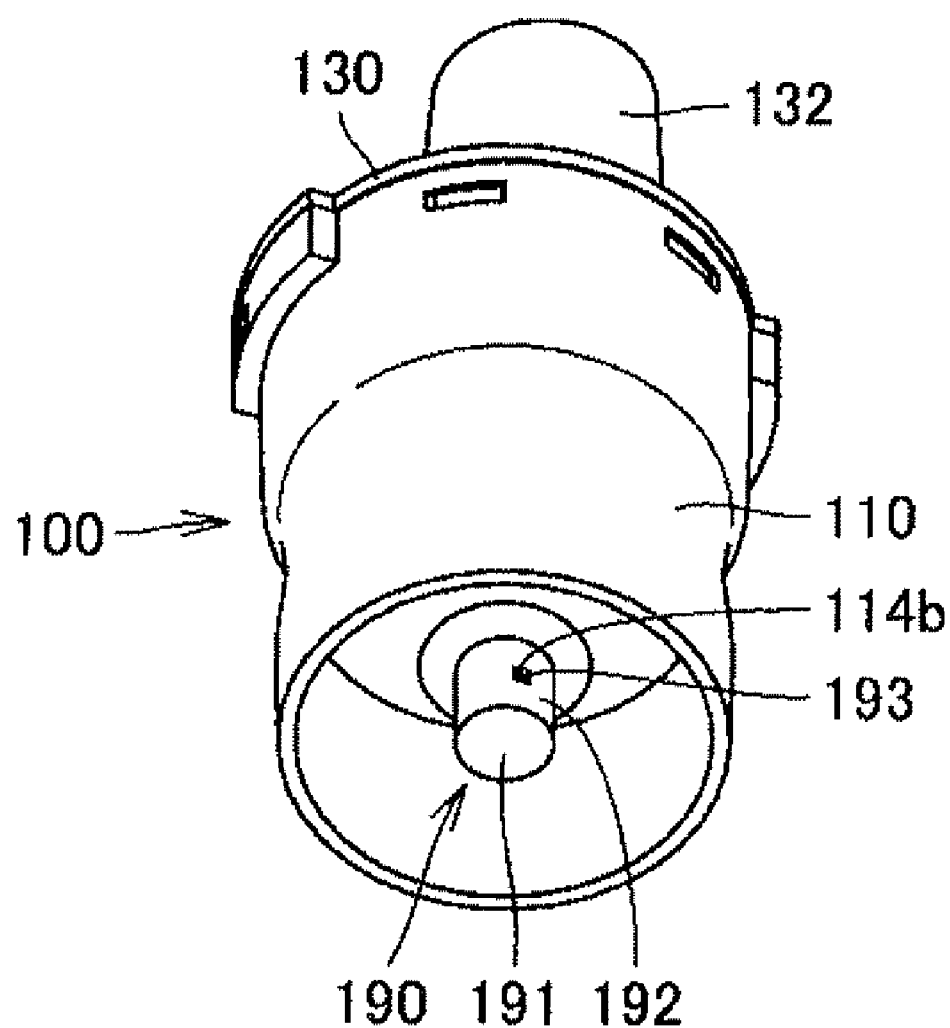
FIG. 26 is a perspective view of the nebulizer body and the blocking member after assembly in the disposal state of the nebulizer of the sixth embodiment of the invention.
Figure 27:
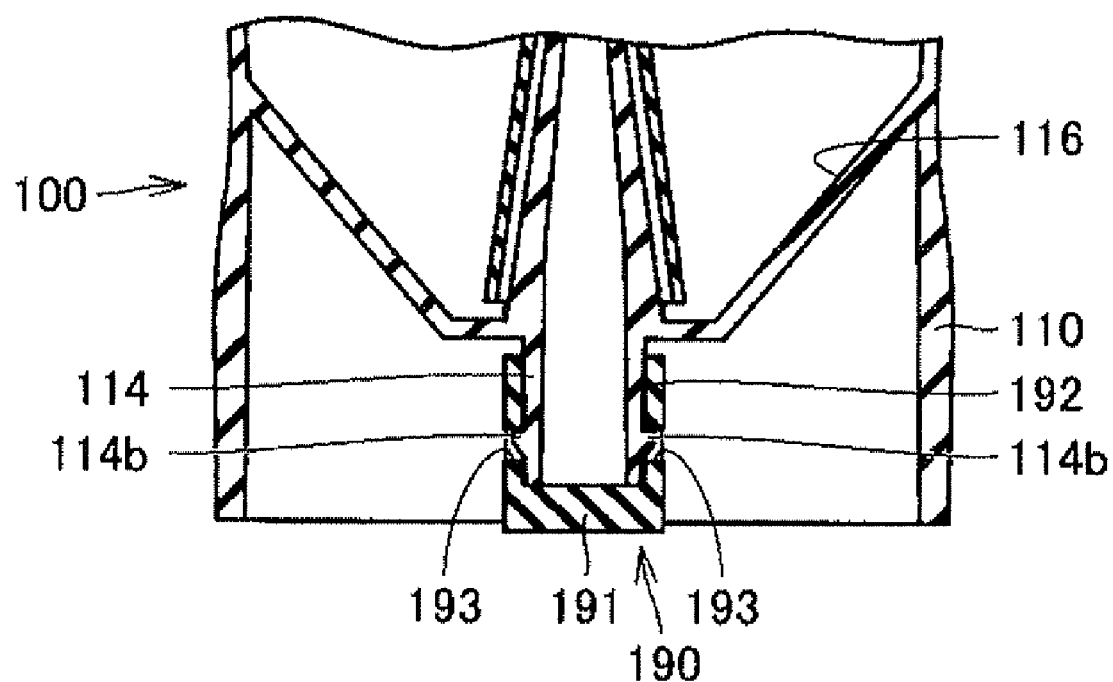
FIG. 27 is an enlarged sectional view illustrating a connection state of a third connection portion and the blocking member after connection in the disposal state of the nebulizer of the sixth embodiment of the invention.

FIG. 25 is an exploded perspective view illustrating an assembly structure of a nebulizer body and a blocking member in a disposal state of a nebulizer according to a sixth embodiment of the invention, and FIG. 26 is a perspective view of the nebulizer body and the blocking member after assembly in the disposal state. FIG. 27 is an enlarged sectional view illustrating a connection state of a third connection portion and the blocking member after connection in the disposal state of the nebulizer of the sixth embodiment. In FIGS. 25 to 27, the component similar to that of the nebulizer 1A of the first embodiment is designated by the same symbol, and the description is not repeated.

As illustrated in FIG. 25, the nebulizer of the sixth embodiment differs slightly from the nebulizer 1A of the first embodiment in the structure of the nebulizer body 100. Specifically, the nebulizer body 100 of the nebulizer of the sixth embodiment does not include the second connection portion 133 that is provided in the nebulizer body 100 of the nebulizer 1A of the first embodiment, and therefore the nebulizer body 100 does not include the latching hole portion 133b that is made in the circumferential surface of the second connection portion 133. The nebulizer body 100 of the nebulizer of the sixth embodiment includes a pair of latching projections 114b in the circumferential surface of the third connection portion 114. The nebulizer of the sixth embodiment includes a cap-shaped blocking member 190 that is independently provided as another component while separated from the nebulizer body 100 and the relay pipe. The blocking member 190 includes a cover portion 191 that is of the blocking portion, a cylindrical wall portion 192 that is vertically provided from the cover portion 191, and a latching projection 193 that is of the pair of latching pawl portions provided at the leading end of the cylindrical wall portion 192. The blocking member 190 is produced by injection molding using a resin material and the like.

In the nebulizer of the sixth embodiment, in the disposal, the third connection portion 114 provided in the nebulizer body 100 is inserted in and connected to the blocking member 190. Therefore, the connection structure between the nebulizer body 100 and the blocking member 190 is realized as illustrated in FIG. 26.

At this point, as illustrated in FIG. 26, in nebulizer body 100 and blocking member 190 which are connected in the disposal state, the compressed air introduction port 114a provided in the nebulizer body 100 is blocked by the cover portion 191 of the blocking member 190. Accordingly, the nebulizer body 100 cannot be used in the disposal state.

The third connection portion 114 and blocking member 190 which are provided in the nebulizer body 100 are connected by the so-called fixed fitting in which the third connection portion 114 and the blocking member 190 cannot substantially be released once are connected. Specifically, as illustrated in FIG. 27, the latching projection 114b provided in the circumferential surface of the third connection portion 114 of the nebulizer body 100 is latched in the latching hole portion 193 made in the circumferential surface of the cylindrical wall portion 192 of the blocking member 190, thereby connecting the third connection portion 114 and blocking member 190 which are provided in the nebulizer body 100. More particularly, part of the latching projection 114b acts as the hook-like latching pawl portion, part of the latching hole portion 193 acts as the latching step portion, and the latching pawl portion is fitted in the latching step portion. Therefore, the fitting cannot be released, and the fixed fitting is realized in the latching between the latching projection 114b and the latching hole portion 193.

Once the nebulizer becomes the disposal state as illustrated in FIG. 26, because the state in which the compressed air introduction port 114a is blocked cannot substantially be released, the nebulizer body 100 cannot be reused after the usage. Accordingly, in the nebulizer of the sixth embodiment, the adoption of the configurations can prohibit the reuse of the nebulizer body 100 after the usage by the simple manipulation, and the generation of the health problem such as the secondary infection can be prevented before happens.

Figure 28:
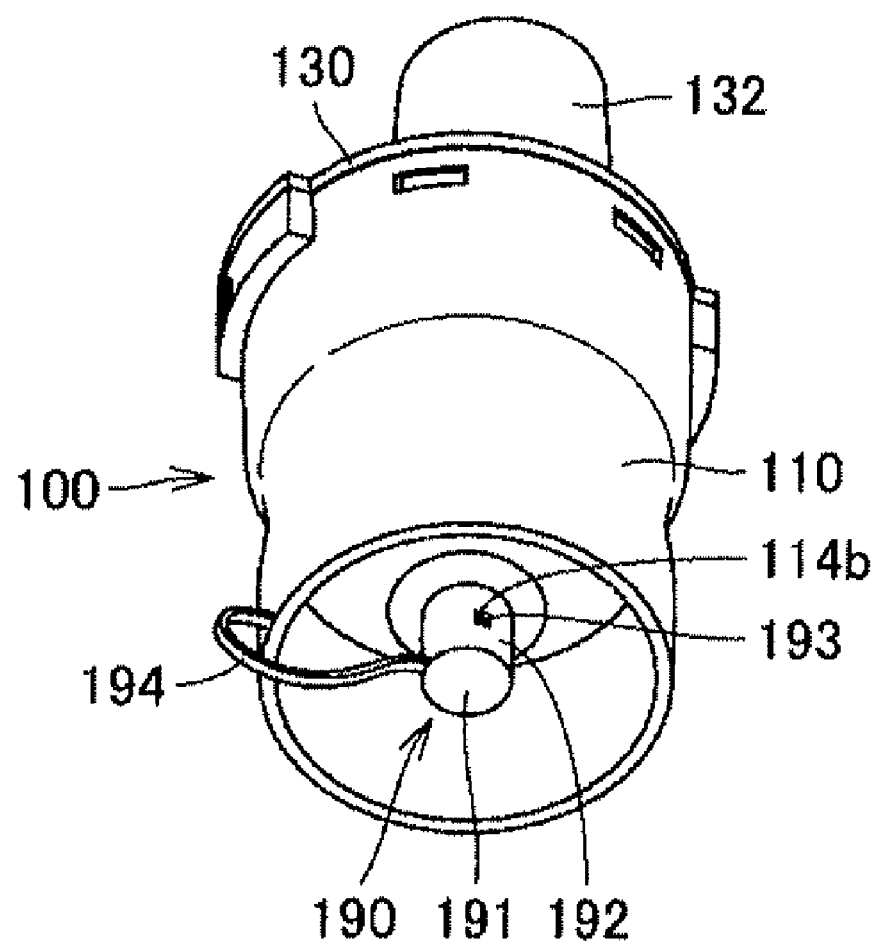
FIG. 28 is a perspective view of a nebulizer body after assembly in a disposal state of a nebulizer according to a modification of the sixth embodiment of the invention.

FIG. 28 is a perspective view of a nebulizer body after assembly in a disposal state for the purpose of description of a modification of the nebulizer of the sixth embodiment.

In the modification illustrated in FIG. 28, the nebulizer body 100 and blocking member 190 of the sixth embodiment are integrally formed. Specifically, a deformable coupling portion 194 that is extended in a thin rod shape is projected from the circumferential surface of the case body 110 of the nebulizer body 100, and the blocking member 190 is formed at the leading end of the coupling portion 194. For the configuration of the modification, advantageously the problem with the loss of the blocking member 190 in advance of the disposal can be prevented before happened in addition to the effect of the fifth embodiment.

Seventh Embodiment

Figure 29:
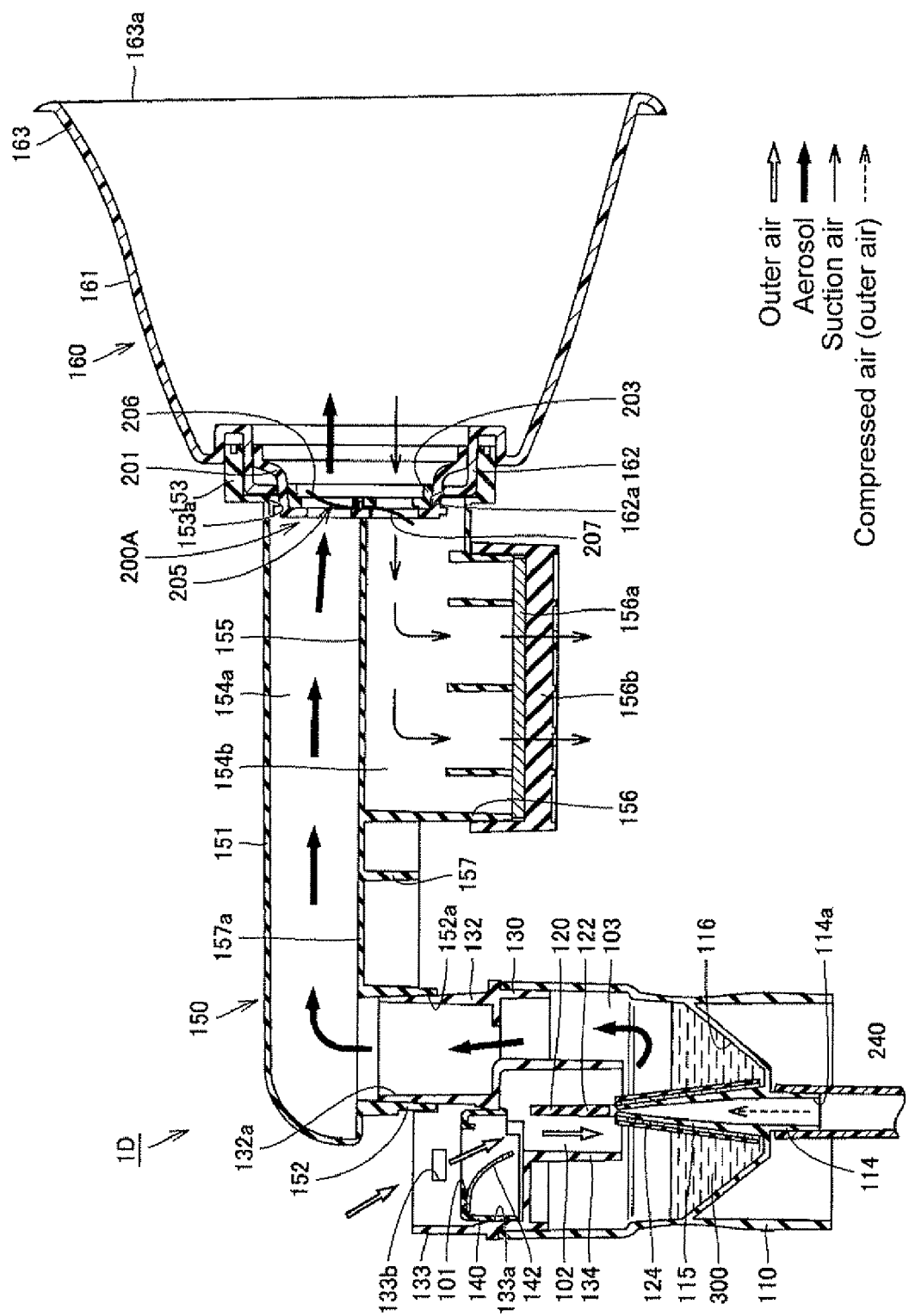
FIG. 29 is a longitudinal sectional view illustrating an internal structure of a nebulizer according to a seventh embodiment of the invention.
Figure 30:
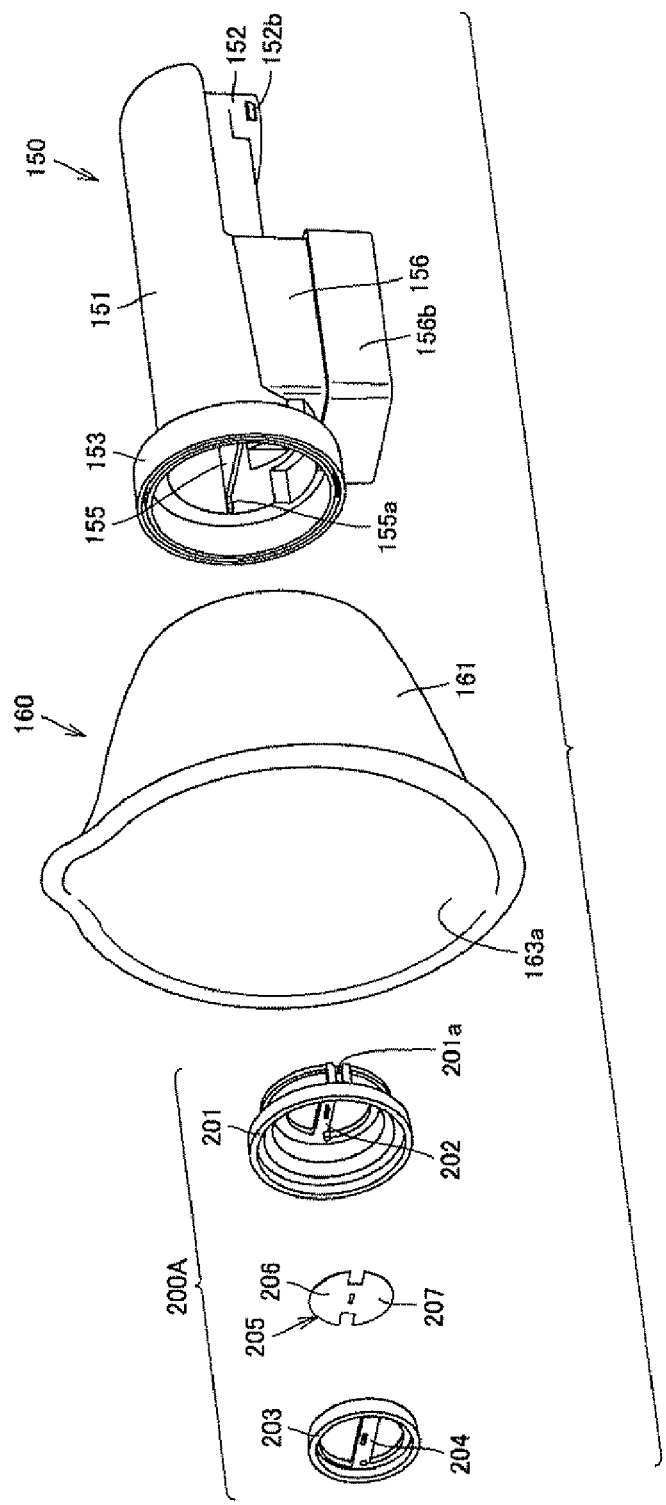
FIG. 30 is an exploded perspective view illustrating an assembly structure of a relay pipe, a mask, and a backflow prevention member of the nebulizer of the seventh embodiment of the invention.
Figure 31:
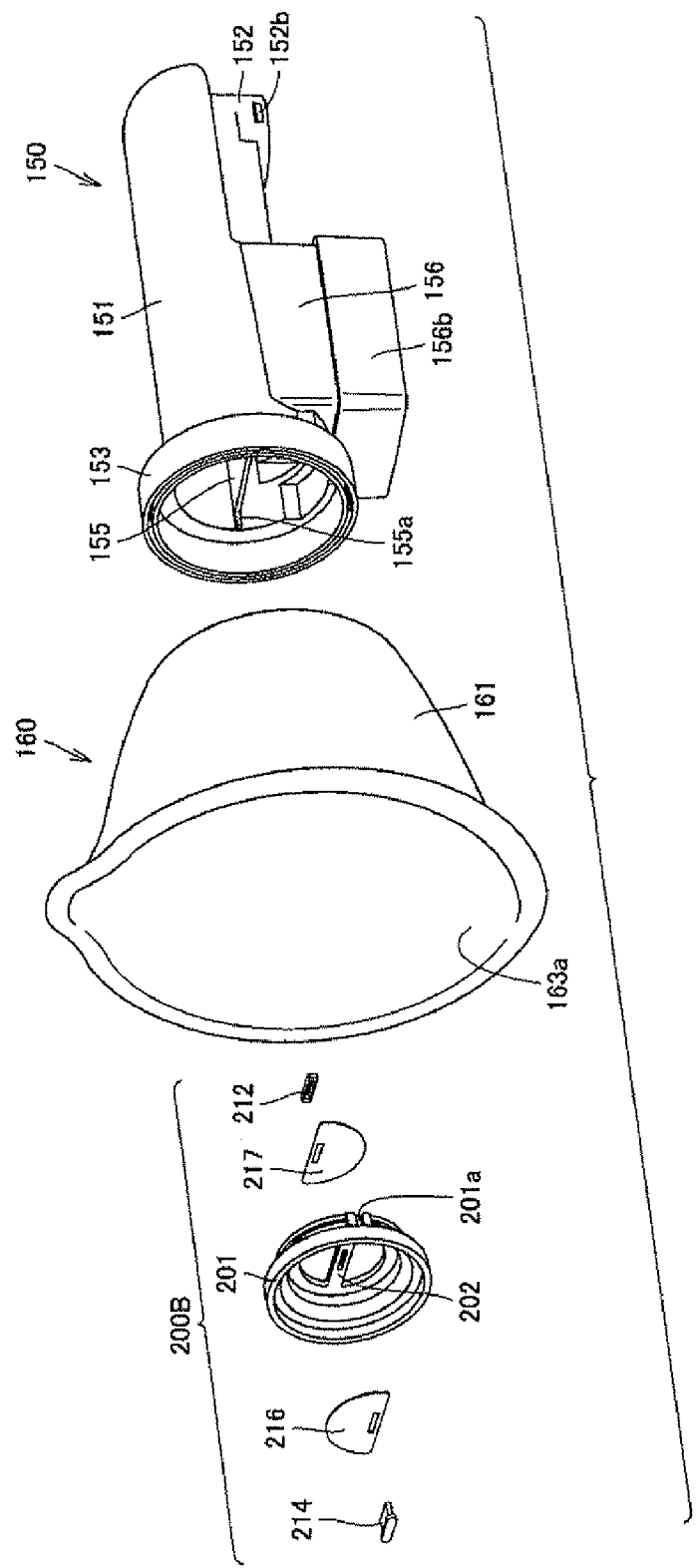
FIG. 31 is an exploded perspective view illustrating an assembly structure of a relay pipe, a mask, and a backflow prevention member of a nebulizer according to a modification of the seventh embodiment of the invention.

FIG. 29 is a longitudinal sectional view illustrating an internal structure of a nebulizer according to a seventh embodiment of the invention, and FIG. 30 is an exploded perspective view illustrating an assembly structure of a relay pipe, a mask, and a backflow prevention member of the nebulizer of the seventh embodiment. In FIGS. 29 and 30, the component similar to that of the nebulizer 1A of the first embodiment is designated by the same symbol, and the description is not repeated.

As described above, in the nebulizer used in the usage environment such as the mass immunization, when the user coughs or sneezes during the administration of the vaccine, there is a risk that the saliva or snivel does not remain in the mask but reaches in the relay pipe or nebulizer body. A nebulizer 1D of the seventh embodiment is configured to prevent the saliva or snivel from reaching the inside of the relay pipe or nebulizer body as much as possible, and the later-described backflow prevention member is used to achieve the solution of the problem.

As illustrated in FIGS. 29 and 30, in the nebulizer 1D of the seventh embodiment, a backflow prevention member 200A is attached to the connection portion between the relay pipe 150 and the mask 160, The backflow prevention member 200A includes a short cylindrical frame body 201 in which a pair of opening portions is formed in the bottom surface, a valve body 205 that is attached to the frame body 201 so as to block the pair of openings provided in the frame body 201, and a short cylindrical fixing member 203 that fixes the valve body 205 to the frame body 201. A pair of opening portions is also formed in the bottom surface of the fixing member 203.

As illustrated in FIG. 30, a projection 202 provided in a central portion of the bottom surface of the frame body 201 is inserted in a hole 208 made in a central portion of the valve body 205, and the valve body 205 is assembled so as to be sandwiched between the frame body 201 and the fixing member 203, thereby forming the frame body 201, the valve body 205, and the fixing member 203 into one member. The backflow prevention member 200A including the frame body 201, the valve body 205, and the fixing member 203 is attached to the relay pipe 150 from the side of the user-side opening portion 163 of the mask 160. More specifically, a groove 201a provided in the circumferential surface of the frame body 201 of the backflow prevention member 200A is pressed in the projection 155a provided at a predetermined position of the partition wall 155 of the relay pipe 150, whereby the mask 160 is assembled while sandwiched between the relay pipe 150 and the backflow prevention member 200A.

As illustrated in FIG. 29, the valve body 205 includes a first valve portion 206 that is disposed according to the conveyance passage 154a of the relay pipe 150 and a second valve portion 207 that is disposed according to the discharge passage 154b of the relay pipe 150. The circumferential edge of the first valve portion 206 of the valve body 205 abuts on the bottom surface of the frame body 201, whereby the first valve portion 206 acts as the check valve in which the bending only toward the side of the mask 160 is permitted. The circumferential edge of the second valve portion 207 of the valve body 205 abuts on the bottom surface of the fixing member 203, whereby the second valve portion 207 acts as the check valve in which the bending only toward the side of the relay pipe 150 is permitted. That is, the backflow prevention member 200A permits only the air current toward the mask 160 from the conveyance passage 154a of the relay pipe 150 while cutting off the air current toward the opposite direction, and the backflow prevention member 200A permits only the air current from the mask 160 toward the discharge passage 154b of the relay pipe 150 while cutting off the air current toward the opposite direction.

Even if the user coughs or sneezes during the administration of the vaccine, the saliva or snivel can be prevented from reaching the inside of the relay pipe 150 or nebulizer body 100 by providing the backflow prevention member 200A in the connection portion between the relay pipe 150 and the mask 160.

FIG. 31 is an exploded perspective view illustrating an assembly structure of a relay pipe, a mask, and a backflow prevention member in a modification of the nebulizer of the seventh embodiment. In the nebulizer 1D of the seventh embodiment, the first valve portion 206 and the second valve portion 207 are formed by one valve body 205. On the other hand, in the nebulizer of the modification, as illustrated in FIG. 31, the first valve portion and second valve portion which are provided in a backflow prevention member 200B are separately formed by valve bodies 216 and 217. In the modification, through-holes are made in the bottom surface of the frame body 201 and the valve bodies 216 and 217, respectively, and fixing members 212 and 214 are fitted in the frame body so as to be inserted in the through-holes, whereby the backflow prevention member 200B is formed as one member. The effect similar to that of the seventh embodiment can be obtained in the configuration of the modification.

The characteristic configurations of the first to seventh embodiments of the invention and the modifications thereof can be combined with each other. For example, the backflow prevention members illustrated in the seventh embodiment of the invention and the modification thereof can be applied to the nebulizers illustrated in the first to sixth embodiments of the invention and the modifications thereof.

In the first to seventh embodiments of the invention and the modifications thereof, at least one of the outer air introduction port, compressed air introduction port, and aerosol lead-out port, which are provided in the nebulizer body, and the aerosol introduction port which is provided in the relay pipe is blocked by the blocking portion so as to be not able to be released, whereby the nebulizer body and/or relay pipe cannot be reused by way of example. Alternatively, obviously the aerosol ejection port of the relay pipe is blocked by the blocking portion so as to be not able to be released, whereby the relay pipe cannot be reused. In such cases, for example, the relay pipe is formed based on the configuration of the fourth embodiment.

In the first to seventh embodiments of the invention and the modifications thereof, the invention is applied to the so-called compressor type nebulizer that produces the aerosol using the compressed air from the compressor and the inhalation aid used in the compressor type nebulizer by way of example. However, the configuration of the fourth embodiment intended to prevent the reuse of the relay pipe or the configuration of the seventh embodiment intended to prevent the saliva or snivel from reaching the relay pipe or nebulizer body can directly be applied to other types of nebulizers and the inhalation aids used therein. That is, the application target of the invention is not limited to the compressor type nebulizer and the inhalation aid used therein, but the invention can be applied to other types of nebulizers and the inhalation aids used therein.

A so-called ultrasonic type nebulizer and a so-called ultrasonic-mesh type nebulizer correspond to other types of nebulizers described above. In the ultrasonic type nebulizer, a high-frequency vibration is provided to the liquid by driving an ultrasonic element, and cavitation generated by the high-frequency vibration is utilized to form the atomized particles from the liquid. In the ultrasonic-mesh type nebulizer, a vibration element and a mesh member are disposed opposite to each other, the liquid is supplied between the vibration element and the mesh member, a vibration is provided to the liquid by driving the vibration element, and the fine liquid is formed by passing the liquid through holes made in the mesh, thereby obtaining the atomized particles. In the ultrasonic type nebulizer and the ultrasonic-mesh type nebulizer, the relay pipe and mask that are of the inhalation aids thereof are formed like the configuration of the fourth embodiment, which allows the reuse of the relay pipe to be prevented. Further, the saliva or snivel can be prevented from reaching the relay pipe or nebulizer body by applying the configuration of the seventh embodiment to the connection portion between the relay pipe and the mask.

The embodiments are disclosed only by way of example and are not restrictive. The technical scope of the invention is defined only by claims, and the technical scope of the invention includes the meanings equal to the descriptions of claims and all changes within claims.

The invention claimed is:

1. A nebulizer comprising:
a nebulizer body in which aerosol is produced; and
an inhalation aid that is used while attached to the nebulizer body in order that a user inhales the aerosol produced in the nebulizer body,
wherein the nebulizer includes:
a reservoir portion in which a liquid is reserved;
a compressed air introduction port that introduces compressed air;
an outer air introduction port that introduces outer air;
an aerosol producing portion that atomizes the liquid reserved in the reservoir portion into atomized particles using the compressed air introduced from the compressed air introduction port and produces aerosol by providing the atomized particles to the outer air introduced from the outer air introduction port; and
an aerosol lead-out port that leads out the aerosol produced in the aerosol producing portion,
the inhalation aid includes:
an aerosol introduction port that introduces the aerosol; and
an aerosol ejection port that ejects the aerosol introduced from the aerosol introduction port toward a user,
the nebulizer body the inhalation aid are detachably connected such that the aerosol lead-out port and the aerosol introduction port are communicated,
the nebulizer further comprises a blocking portion that can block at least one of the compressed air introduction port, the outer air introduction port, the aerosol lead-out port, the aerosol introduction, port, and the aerosol ejection port, and
the blockage of the blocking portion cannot substantially be released once the blockage is performed by the blocking portion.

2. The nebulizer according to claim 1, wherein the blocking portion is formed by a cap-shaped member that is independently provided as another component while separated from the nebulizer body and the inhalation aid.

3. The nebulizer according to claim 1, wherein the blocking portion is formed by a cap-shaped member that is provided in one of the nebulizer body and the inhalation aid.

4. The nebulizer according to claim 3, wherein the blocking portion is attached to one of the nebulizer body and the inhalation aid a deformable coupling portion interposed therebetween.

5. The nebulizer according to claim 1, comprising a latching mechanism that includes a latching pawl portion provided in one of the nebulizer body and the blocking portion and a latching step portion provided in the other of the nebulizer body and the blocking portion,
the latching pawl portion is fitted in the latching step portion while being not able to be detached from the latching step portion, and the blocking portion is connected to the nebulizer body while being not able to be detached from the nebulizer body, whereby the blockage of the blocking portion cannot substantially be released.

6. The nebulizer according to claim 1, comprising a latching mechanism that includes a latching pawl portion provided in one of the inhalation aid and the blocking portion and a latching step portion provided in the other of the inhalation aid and the blocking portion,
the latching pawl portion is fitted in the latching step portion while being not able to be detached from the latching step portion, and the blocking portion is connected to the inhalation aid while being not able to be detached from the inhalation aid aid, whereby the blockage of the blocking portion cannot substantially be released.

7. A nebulizer comprising:
a nebulizer body in which aerosol is produced; and
an inhalation aid that is used while attached to the nebulizer body in order that a user inhales the aerosol produced in the nebulizer body.
wherein the nebulizer body includes:
a reservoir portion in which a liquid is reserved;
a compressed air introduction port that introduces compressed air;
an outer air introduction port that introduces outer air;
an aerosol producing portion that atomizes the liquid reserved in the reservoir portion into atomized particles using the compressed air introduced from the compressed air introduction port and produces aerosol by providing the atomized particles to the outer air introduced from the outer air introduction port; and
an aerosol lead-out port that leads out the aerosol produced in the aerosol producing portion,
the inhalation aid includes:
an aerosol introduction port that introduces the aerosol; and
an aerosol ejection port that ejects the aerosol introduced from the aerosol introduction port toward a user,
the nebulizer body and the inhalation aids take a first connection state in which the inhalation aid is detachably connected to the nebulizer body and a second connection state in which the inhalation aid is connected to the nebulizer body while being not able to be detached from the nebulizer body,
the aerosol introduction port and the aerosol lead-out port are communicated in the first connection state, and
at least one of the compressed air introduction port, the outer air introduction port, and the aerosol lead-out port is blocked by the inhalation aid in the second connection state.

8. The nebulizer according to claim 7, wherein a cap-shaped member that blocks one of the compressed air introduction port, the outer air introduction port, and the aerosol lead-out port in the second state is provided in the inhalation aid.

9. The nebulizer according to claim 7, comprising a latching mechanism that includes a latching pawl portion provided in one of the nebulizer body and the inhalation aid and a latching step portion provided in the other of the nebulizer body and the inhalation aid and,
the latching pawl portion is fitted in the latching step portion while being not able to be detached from the latching step portion in the second connection state, whereby the inhalation aid is connected to the nebulizer body while being not able to be detached from the nebulizer body.

10. An inhalation aid that is used while detachably attached to the nebulizer body in order that a user inhales the aerosol produced in the nebulizer body,
the inhalation aid comprising:
a aerosol introduction port that introduces aerosol from the nebulizer body;
an aerosol ejection port that ejects the aerosol introduced from the aerosol introduction port toward the user; and
a blocking portion that can block at least one of the aerosol introduction port and the aerosol ejection port, and
the blockage of the blocking portion cannot substantially be released once the blockage is performed by the blocking portion.

11. The inhalation aid according to claim 10, wherein the blocking portion is formed by a cap-shaped member that is independently provided as another component while separated from the inhalation aid.

12. The inhalation aid according to claim 10, wherein the blocking portion is attached to the inhalation aid with a deformable coupling portion interposed therebetween.

13. The inhalation aid according to claim 10, further comprising a latching mechanism that includes a latching pawl portion provided in one of the blocking portion and a portion except the blocking portion and a latching step portion provided in the other of the blocking portion and the portion except the blocking portion,
the latching pawl portion is fitted in the latching step portion while being not able to be detached from the latching step portion, and the blocking portion is connected to the portion except the blocking portion while being not able to be detached from the portion except the blocking portion, whereby the blockage of the blocking portion cannot substantially be released.

* * * * *